United States Patent
Anderson et al.

(10) Patent No.: US 9,114,114 B2
(45) Date of Patent: Aug. 25, 2015

(54) EDIBLE PRODUCTS HAVING A HIGH COCOA POLYPHENOL CONTENT AND IMPROVED FLAVOR AND THE MILLED COCOA EXTRACTS USED THEREIN

(75) Inventors: Brent A. Anderson, Lincoln Park, NJ (US); John M. Kaiser, Manheim, PA (US); Ilene K. Cooper, Mount Joy, PA (US); David J. Hausman, Lancaster, PA (US); Barry D. Glazier, Harrisburg, PA (US); Jacqueline B. Kramer, Stroudsburg, PA (US); Tracey L. Knapp, E. Stroudsburg, PA (US)

(73) Assignee: MARS, INC., McLean, VA (US)

( * ) Notice: Subject to any disclaimer, the term of this patent is extended or adjusted under 35 U.S.C. 154(b) by 1574 days.

(21) Appl. No.: 11/766,224

(22) Filed: Jun. 21, 2007

(65) Prior Publication Data

US 2008/0317891 A1  Dec. 25, 2008

(51) Int. Cl.
| | |
|---|---|
| A61K 36/185 | (2006.01) |
| A21D 13/08 | (2006.01) |
| A23G 1/32 | (2006.01) |
| A23G 1/46 | (2006.01) |
| A23G 1/56 | (2006.01) |
| A23G 3/48 | (2006.01) |
| A23L 1/164 | (2006.01) |
| A23L 1/30 | (2006.01) |
| A23L 1/38 | (2006.01) |

(52) U.S. Cl.
CPC .............. *A61K 36/185* (2013.01); *A21D 13/08* (2013.01); *A23G 1/32* (2013.01); *A23G 1/46* (2013.01); *A23G 1/56* (2013.01); *A23G 3/48* (2013.01); *A23L 1/1643* (2013.01); *A23L 1/3002* (2013.01); *A23L 1/38* (2013.01); *A23V 2002/00* (2013.01)

(58) Field of Classification Search
None
See application file for complete search history.

(56) References Cited

U.S. PATENT DOCUMENTS

| | | |
|---|---|---|
| 1,925,326 A | 9/1933 | Kellogg et al. |
| 2,380,158 A | 7/1945 | Durrenmatt et al. |
| 2,512,663 A | 6/1950 | Masurovsky |
| 2,515,794 A | 7/1950 | Palmer |
| 2,823,124 A | 2/1958 | Heden |
| 2,835,585 A | 5/1958 | Russoff |
| 2,954,293 A | 9/1960 | Russoff |
| 2,957,169 A | 10/1960 | Rusoff |
| 3,559,895 A | 2/1971 | Fay |
| 3,615,659 A | 10/1971 | Weber |
| 4,156,030 A | 5/1979 | Eggen |
| 4,189,102 A | 2/1980 | Andrews |
| 4,224,354 A * | 9/1980 | Szegvari ........................ 426/584 |
| 4,281,027 A | 7/1981 | Inoue et al. |
| 4,343,818 A | 8/1982 | Eggen |
| 4,390,698 A | 6/1983 | Chiovini et al. |
| 4,407,834 A | 10/1983 | Chiovini et al. |
| 4,444,798 A | 4/1984 | Magnolato et al. |
| 4,504,017 A | 3/1985 | Andrews |
| 4,532,147 A | 7/1985 | Jonas et al. |
| 4,758,444 A | 7/1988 | Terauchi et al. |
| 4,807,815 A | 2/1989 | Csillag et al. |
| 4,908,212 A | 3/1990 | Kwon et al. |
| 4,956,429 A | 9/1990 | Harmetz et al. |
| 4,970,090 A | 11/1990 | Zeiger et al. |
| 5,338,554 A | 8/1994 | Vogt et al. |
| 5,554,645 A | 9/1996 | Romanczyk, Jr. et al. |
| 5,637,344 A | 6/1997 | Carpenter et al. |
| 5,912,363 A | 6/1999 | Nafisi-Movaghar et al. |
| 6,007,857 A | 12/1999 | Kimura et al. |
| 6,015,913 A | 1/2000 | Kealey et al. |
| 6,194,020 B1 * | 2/2001 | Myers et al. .................. 426/631 |
| 6,207,702 B1 | 3/2001 | Schmitz et al. |
| 6,265,593 B1 | 7/2001 | Best et al. |
| 6,297,273 B1 | 10/2001 | Romanczyk, Jr. et al. |
| 6,312,753 B1 | 11/2001 | Kealey et al. |
| 6,576,275 B1 | 6/2003 | Hoving et al. |
| 6,610,320 B2 | 8/2003 | Schmitz et al. |
| 6,627,232 B1 | 9/2003 | Hammerstone, Jr. et al. |
| 6,743,450 B2 | 6/2004 | Romanczyk, Jr. et al. |
| 6,805,883 B2 | 10/2004 | Chevaux et al. |

(Continued)

FOREIGN PATENT DOCUMENTS

| | | |
|---|---|---|
| DE | 2 055 030 | 5/1972 |
| EP | 0906761 | 4/1999 |

(Continued)

OTHER PUBLICATIONS

J. Clapperton, et al., "Polyphenols and cocoa flavour", Proceedings of the XVIth International Conference of the Groupe Polyphenols, Jul. 13-16, 1992, Lisbon, Portugal.

Cook, L. Russell et al., "Chocolate production and use", pp. 72-75, Published by Harcourt Brace Jovanovich, Inc., New York, NY (1982).

(Continued)

*Primary Examiner* — Terry McKelvey
*Assistant Examiner* — Catheryne Chen
(74) *Attorney, Agent, or Firm* — Nath, Goldberg & Meyer; Scott H. Blackman

(57) ABSTRACT

Milling dry extracts containing cocoa polyphenols (CPs) to reduce the particle size improves the flavor of edible products (e.g., foods, medical foods, nutritional supplements, and pharmaceuticals) or additives containing the milled cocoa extracts. The products, e.g., chocolates, are less astringent and less bitter. The mean particle size after milling is less than about 15 microns, preferably less than about 10 microns, and most preferably less than about 5 microns. The total CP content of the milled extracts is at least about 300 milligrams and preferably about 300 to about 700 milligrams per gram of milled extract. The additives consist essentially of (i) the milled high CP cocoa extract and (ii) a fat (e.g., cocoa butter), an oil (e.g., vegetable oil), or a syrup (e.g., corn syrup).

17 Claims, 9 Drawing Sheets

(56) References Cited

U.S. PATENT DOCUMENTS

| | | |
|---|---|---|
| 7,968,140 B2 | 6/2011 | Kealey et al. |
| 2002/0001651 A1 | 1/2002 | Norris et al. |
| 2003/0129269 A1 | 7/2003 | Lee et al. |
| 2003/0170199 A1 | 9/2003 | Leclere |
| 2003/0206981 A1 | 11/2003 | Lee et al. |
| 2003/0211184 A1 | 11/2003 | Hoving et al. |
| 2003/0215558 A1 | 11/2003 | Kealey et al. |
| 2004/0005347 A1 | 1/2004 | Ter Laak et al. |
| 2004/0096566 A1 | 5/2004 | Lecoupeau et al. |
| 2004/0224906 A1 | 11/2004 | Hoving et al. |
| 2005/0031762 A1 | 2/2005 | McCarthy |
| 2005/0069625 A1 | 3/2005 | Chimel et al. |
| 2005/0074521 A1 | 4/2005 | Bartnick et al. |
| 2005/0152852 A1 | 7/2005 | Nishimura et al. |
| 2006/0117965 A1* | 6/2006 | Parsons et al. ............ 99/495 |
| 2006/0269633 A1 | 11/2006 | Kapp et al. |
| 2007/0054030 A1* | 3/2007 | Peterson et al. ........... 426/631 |
| 2007/0077318 A1 | 4/2007 | Pons-Andreu et al. |
| 2007/0219146 A1 | 9/2007 | Rhaskaran et al. |
| 2007/0292577 A1 | 12/2007 | Kopp et al. |

FOREIGN PATENT DOCUMENTS

| | | |
|---|---|---|
| EP | 1 026 164 | 8/2000 |
| EP | 1 304 047 | 4/2003 |
| EP | 1 728 434 | 5/2005 |
| EP | 1 346 640 | 5/2007 |
| EP | 2071961 A1 | 6/2009 |
| FR | 2838055 | 10/2003 |
| GB | 751 121 | 6/1956 |
| GB | 2 011 239 | 7/1978 |
| GB | 2 223 944 | 4/1990 |
| GB | 2 410 172 | 7/2005 |
| GB | 2 414 393 | 11/2005 |
| JP | 403094640 | 4/1991 |
| JP | 05184298 | 7/1993 |
| JP | HEI 7-213251 | 8/1995 |
| JP | 07-274894 | 10/1995 |
| JP | 7274894 | 10/1995 |
| JP | 9-206026 | 8/1997 |
| JP | 9-224606 | 9/1997 |
| JP | 9-234018 | 9/1997 |
| JP | 11308978 | 11/1999 |
| JP | 2002-128685 | 5/2002 |
| JP | 2002-153213 | 5/2002 |
| JP | 2003-137800 | 5/2003 |
| JP | 2005-304332 | 11/2005 |
| WO | WO97/36597 | 10/1997 |
| WO | 9945797 A1 | 9/1999 |
| WO | WO 00/02460 * | 1/2000 |
| WO | 0145726 A2 | 6/2001 |
| WO | WO01/91590 | 12/2001 |
| WO | WO 02/14251 | 2/2002 |
| WO | WO 03/077668 | 9/2003 |
| WO | WO 03/091237 | 11/2003 |
| WO | WO 2005/034648 | 4/2005 |
| WO | 2005077197 A1 | 8/2005 |
| WO | WO 2005/115160 A1 * | 12/2005 |
| WO | WO2006/079731 | 8/2006 |
| WO | WO 2006/117416 | 11/2006 |
| WO | 2007002852 A2 | 1/2007 |
| WO | WO2007/062206 | 5/2007 |
| WO | WO2007/082703 | 7/2007 |
| WO | WO2007/098205 | 8/2007 |
| WO | WO 2007/106473 | 9/2007 |

OTHER PUBLICATIONS

Counet, et al., "Effect of the number of flavanol units on the antioxidant activity of procyanidin fractions isolated from chocolate", J. Agric. Food Chem., pp. 6816-6822 (2003).
W.G.C. Forsyth, "*Cacao* Polyphenolic Substances.1. Fractionation of the Fresh Bean", Biochem J., 51(4): 511-516 (1952).
W.G.C. Forsyth, "*Cacao* Polyphenolic Substances.2. Changes During Fermentation", Biochem J., 51(4): 516-520 (1952).
W.G.C. Forsyth, "*Cacao* Polyphenolic Substances. 3. Separation and Estimation on Paper Chromatograms", Biochem J., 60(1): 108-111 (1955).
L.A. Griffiths, "A Comparative Study of the Seed Polyphenols of the Genus *Theobroma*", Biochem J., 74:362-365. (1960).
M.A.F. Jalal, et al., "Polyphenols of mature plant, seedling and tissue cultures of *Theobroma cacao*", Phytochem. 16: 1377-1380 (1977).
H. Kim, et al., "(-)-Epicatechin Content in Fermented and Unfermented Cocoa Beans", J. Food Sci. 49:1090-1092 (1984).
M.C. Lee, et al., "Investigation of the chemical structure of the polyphenol compound extracted from *Cacao* bean", Agri. Chem. And Bio. 41:110-117 (1998).
L.J. Porter, et al., "*Cacao* procyanidins: major flavanoids and identification of some minor metabolites", Phytochem., v. 30(5):1657-1663 (1991).
J. Rigaud, et al., "Normal-phase high-performance liquid chromatographic separation of procyanidins from *cacao* beans and grape seeds", J. Chromatog. A., 654: 255-260 (1993).
G. Zieglander, et al., "Antioxidative effects of cocoa", CCB: Review for Chocolate, Confectionery and Bakery, 8:3-6 (1983).
U. Bracco et al., JAOCS Jun. 1981 686-690.
E. Cros et al., Café*Cacao* Thé Apr.-Jun. 1982 XXVI (2): 109-114 & Translation.
M.M. De Oliveira et al., An. Acad. brasil Cienc. 1978 44(1): 41-44.
W.G.C. Forsyth et al., Biochem. J. 1960 pp. 374-378.
H. Kim et al., 37th P.M.C.A. Production Conference 1983 pp. 60-63.
H. Kim et al., J. Food Sci. 1983 48(2): 548-551.
S. Naito et al., J. Japan Society for Food Eng. 1982 29(9): 529-533.
T. Osawa, 1st Intl. Symp. on Chocolate and Cocoa Nutrition Tokyo Sep. 27, 1995 pp. 5-7.
V. J. Paolino et al., Arch. oral Biol. 1985 30(4): 359-363.
G. L. Pettipher, Food Agric. 1986 37: 297-309.
J. Salmonowicz et al., Intl. Symp. on Deterioration of Lipids, Gdansk 1971 pp. 215-219.
Translation of K. Shimizu et al., Nippon Sho. Kag. Kog. Kaishi 2001 48(4):238-245.
F. Villeneuve et al., Café*Cacao* Thé Jul.-Sep. 1989 XXXIII (3):165-169 and Translation.
A.L. Whaterhouse et al., Lancet Sep. 21, 1996 348(9030) 834.
Translation of N. Yamaguchi et al., New Food Industry 1984 25(1)68-71 and Translation.
A. Zumbe, BNF Nutrition Bulletin Spring 1998 23:94-102.

\* cited by examiner

EDIBLE PRODUCTS HAVING A HIGH COCOA POLYPHENOL CONTENT AND IMPROVED FLAVOR AND THE MILLED COCOA EXTRACTS USED THEREIN

CROSS REFERENCE TO RELATED APPLICATIONS

None.

BACKGROUND OF THE INVENTION (1) Field of the Invention

The present invention relates to cocoa extracts having a reduced particle size, and to products such as foods, dietary supplements, and pharmaceuticals containing the reduced particle size cocoa extracts or additives containing the reduced particle size cocoa extracts.

(2) Description of Related Art

Polyphenolic compounds are bioactive substances that are derived from plant materials. They are closely associated with the sensory and nutritional quality of products derived from these plant materials. Many plant polyphenols have an antioxidant activity and numerous health benefits. Consumption of cocoa polyphenols (CPs) in cocoa products provides significant health benefits. Cocoa polyphenols have been shown to have beneficial effects on the processes believed to be involved in the development of atherosclerosis and cardiovascular disease. Cocoa polyphenols inhibit LDL oxidation, enhance nitric oxide/nitric oxide synthase (NO/NOS) activity, and inhibit cyclo-oxygenase (COX) and lipoxygenase (LOX) activity; these effects are reported in WO 97/36497 published Oct. 9, 1997. Cocoa polyphenols can also be used to treat or prevent conditions which are known to be affected by the administration of non-steroidal anti-inflammatory drugs, for example, aspirin.

The term "cocoa polyphenols" refers to the polyphenolic compounds, including proanthocyanidins, more particularly procyanidins, present in cocoa beans, cocoa nibs, and most cocoa ingredients prepared from cocoa beans or cocoa nibs. The term "procyanidin" refers to naturally occurring or synthetically derived oligomers of catechin and/or epicatechin. Any reference to "cocoa polyphenols" should be understood to include the flavan-3-ol monomers catechin and epicatechin. The monomers include (+)-catechin and (−)-epicatechin and their respective epimers (e.g., (+)-epicatechin and (−)-catechin) and derivatives thereof. The monomers have the formula "A" and the oligomers have the formula "$A_n$" where n in an integer from 2 to 18 and higher. "A" has the formula:

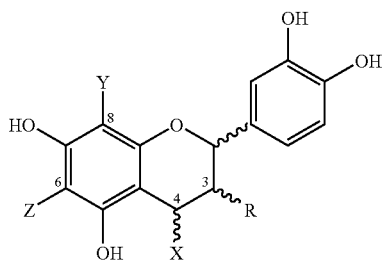

where R is 3-(α)-OH, 3-(β)-OH, 3-(α)-O-saccharide, 3-(β)-O-saccharide, 3-(α)—O—C(O)—$R^1$, or 3-(β)—O—C(O)—$R^1$;

where bonding between adjacent monomers takes place at positions 4 and 6 or 4 and 8;

where a bond to a monomer in position 4 has alpha or beta stereochemistry;

where X, Y, and Z are selected from the group consisting of A, hydrogen, and a saccharide moiety, with the proviso that as to at least one terminal monomer, bonding of the adjacent monomer thereto is at position 4 and optionally Y=Z=hydrogen; and where the saccharide moiety is a mono- or di-saccharide moiety which may be optionally substituted with a phenolic moiety;

where $R^1$ may be an aryl or heteroaryl moiety optionally substituted with at least one hydroxy group; and salts, derivatives, and oxidation products thereof. Advantageously, the saccharide moiety is derived from the group consisting of glucose, xylose, rhamnose, and arabinose. The saccharide moiety and any or all of R, X, Y, and Z may optionally be substituted at any position with a phenolic moiety via an ester bond. The phenolic moiety is selected from the group consisting of caffeic, cinnamic, coumaric, ferulic, gallic, hydroxybenzoic, and sinapic acids.

Cocoa polyphenol extracts, particularly epicatechin, catechin, and procyanidin extracts, have recently been shown to possess significant biological utility. Thus, the consumption of cocoa products having a high cocoa polyphenol content may provide significant health benefits.

Cocoa polyphenol extracts, or compounds further separated therefrom, were initially prepared on a laboratory scale. See U.S. Pat. No. 5,554,645 (Romanczyk et al.) issued Sep. 10, 1996. Solid compositions and liquid preparations containing the cocoa extracts are disclosed in the '645 patent.

Underfermented and unfermented raw cocoa materials contain substantial amounts of cocoa polyphenols compared to fermented cocoa materials. Fermentation and drying bring about complex changes in the cocoa bean, most notably the formation of the components required for the development of the characteristic flavor and color of cocoa. Fermentation, however, also significantly decreases the concentrations of the polyphenolic compounds in the fermented cocoa beans relative to the concentrations of polyphenolic compounds in the unfermented or underfermented cocoa beans. Traditional cocoa bean processing, including such steps as roasting or defatting of the cocoa beans, also reduces the cocoa polyphenol concentration in the cocoa powder or chocolate liquors produced thereby. Moreover, these processes reduce the concentrations of higher oligomeric polyphenols (i.e., oligomers 5-12) more rapidly than the lower oligomers (i.e., oligomers 2-4).

Cocoa extracts containing polyphenols can also be prepared by solvent extracting partially or fully defatted cocoa solids prepared from unfermented and/or underfermented cocoa beans or cocoa nibs. See U.S. Pat. No. 6,015,913 (Kealey et al.) issued Jan. 18, 2000 and U.S. Pat. No. 6,312,753 (Kealey et al.) issued Nov. 6, 2001, the disclosures of which are incorporated herein by reference.

A process for selectively extracting tetramers, pentamers, and higher molecular weight oligomers and monomers and dimers from partially defatted cocoa solids is disclosed in U.S. Pat. No. 6,627,232 (Hammerstone et al.) issued Sep. 30, 2003, the disclosure of which is incorporated herein by reference.

A process for selectively extracting procyanidins from an aqueous mixture of cocoa polyphenols is also disclosed in U.S. 2007-0078261-A1 (Robbins, et al.) published Apr. 5, 2007, the disclosure of which is incorporated herein by reference.

A process for preventing the loss of cocoa polyphenols during the processing of partially defatted or fully defatted cocoa solids into foods or food supplements involves pretreating the cocoa solids with about 9% to about 90% by weight of sterol and/or stanol esters which are liquids at about 80° C. or less or by pre-treating the cocoa solids with about 0.05% to about 5% by weight of a lecithin. See U.S. 2005-0069625-A1 (Chimel et al.) published Mar. 31, 2005, the disclosure of which is incorporated herein by reference.

SUMMARY OF THE INVENTION

In one embodiment, the present invention is directed to a milled cocoa extract having a total cocoa polyphenol content of at least about 300, preferably about 300 to about 700 milligrams, per gram of the milled extract and a reduced particle size. The cocoa extracts are obtained by solvent extracting cocoa beans, also referred to as cacao beans, or the cocoa solids prepared from the cocoa beans or nibs. Preferably the cocoa beans are unfermented and/or underfermented cocoa beans. The mean particle size of the milled extract is less than about 15 microns, preferably less than about 10 microns, and most preferably less than about 5 microns. About 90 volume % of the milled particles are less than about 30 microns, preferably less than about 20 microns, and most preferably less than about 10 microns. Preferably the total cocoa polyphenol content is about 400 milligrams, more preferably about 400 to about 600 milligrams, and most preferably about 400 to about 500 milligrams per gram of the milled cocoa extract.

The cocoa polyphenols in the high CP cocoa extract include, but are not limited to, epicatechin, catechin, and/or procyanidin oligomers thereof. The extract may contain oligomers such as the dimers through at least the decamers and in some cases the undecamers and dodecamers. The extract may be fractionated into monomers or individual oligomers.

In a second embodiment, the present invention is directed to an additive consisting essentially of (i) a fat and/or an oil; (ii) a milled cocoa extract comprising cocoa polyphenols; and (iii) optionally an emulsifier. The fat can be cocoa butter or a milk fat. The oil can be vegetable oil. The fat and/or the oil is present in an amount sufficient to disperse the milled cocoa extract in the fat and/or the oil. The milled cocoa extracts have the total cocoa polyphenol contents and mean particle size particle sizes and/or particle size distributions described above.

In a third embodiment, the present invention is directed to an additive consisting essentially of (i) a syrup comprising water and a nutritive carbohydrate sweetener and/or a sugar substitute; (ii) a milled cocoa extract, and (iii) optionally a fat and/or an oil. The syrup is present in an amount sufficient to disperse the milled cocoa extract in the syrup. The milled cocoa extract has total cocoa polyphenol contents and mean particle sizes and/or particle size distributions discussed above. The nutritive carbohydrate sweetener can be a corn syrup or a blend thereof and another sweetener. Preferably, the fat, if present, is cocoa butter or a milk fat and the oil, if present, is a vegetable oil.

The additives can be used in foods, medical foods, dietary supplements, or pharmaceutical products having a reduced water activity, i.e., a water activity of 0.91 or below, preferably 0.1 to 0.7.

In a fourth embodiment, the present invention is directed to a food, a medical food, a dietary supplement, or a pharmaceutical having a reduced water activity which comprises (i) a milled cocoa extract and (ii) a fat, an oil, and/or a syrup or (ii) an additive consisting essentially of the milled high CP cocoa extract and the fat, the oil, and/or the syrup.

Foods particularly useful herein include confectioneries, cereals, cereal bars, baked goods, puddings, and sauces, and preferably chocolates such as, for example milk chocolate, skim milk chocolate, buttermilk chocolate, mixed diary product chocolate, sweet chocolate, bittersweet chocolate, white chocolate, and reduced fat chocolate.

A chocolate comprising a milled cocoa extract containing at least about 300 milligrams of total cocoa polyphenols per gram of the milled extract is characterized by reduced bitterness, e.g., a reduction of about 0.5 units on a scale of 0 to 15, and reduced astringency, e.g., about 0.5 units, preferably about 0.75 units, and more preferably greater than about 0.75 units on a scale of 0 to 15. The scale used is an art-recognized sensory scale discussed hereafter.

The chocolates are prepared by a process which comprises the steps of:

a. providing a mixture of one or more carbohydrate ingredients, one or more cocoa ingredients, and optionally one or more milk solids-containing ingredients; and b. adding to the ingredient mixture, before, after, or during the conching or tempering, a milled cocoa extract having the total cocoa polyphenol content and particle size distribution discussed above.

The cocoa ingredients which may used in preparing the chocolate include chocolate liquor, alkalized chocolate liquor, partially defatted or fully defatted cocoa solids, alkalized partially or fully defatted cocoa solids, cocoa powder, alkalized cocoa powder, and/or cocoa butter. In some embodiments, chocolate liquor and/or cocoa solids having a high amount of total cocoa polyphenols (CPs) are used in the products to increase total cocoa polyphenol content of the final product. High CP cocoa ingredients are prepared from unfermented and/or underfermented cocoa beans.

Products and additives containing the milled high CP cocoa extracts have an improved flavor, i.e., less astringency and less bitterness, but more importantly their total cocoa polyphenol content is not reduced by the milling used to reduce the particle size. One skilled in the art would expect that by milling bitter or astringent compounds, the compound's increased surface area would cause increased levels of bitterness or astringency, as is observed with caffeine. Surprisingly, when the milled high CP extracts are milled to smaller particle sizes, one sees a reduction in bitterness and astringency. The same flavor improvement does not result when the milled high CP cocoa extracts are added to water or an aqueous-based system such as milk or cream. When added to a chocolate, the astringency and the bitterness are reduced. For example, in a milk chocolate bar containing 150 milligrams of total cocoa polyphenols per a 40 gram serving, the bitterness was reduced by 0.5 unit on a 0 to 15 scale while the astringency was reduced by nearly 0.75 unit on a scale of 0 to 15. These attributes are significantly different at ≤0.10. The attributes are quantified on a standardized intensity scale of 0 to 15, which is discussed hereafter under "Testing Procedures".

DETAILED DESCRIPTION OF THE INVENTION

Selection of Cocoa Beans

Figure 1:
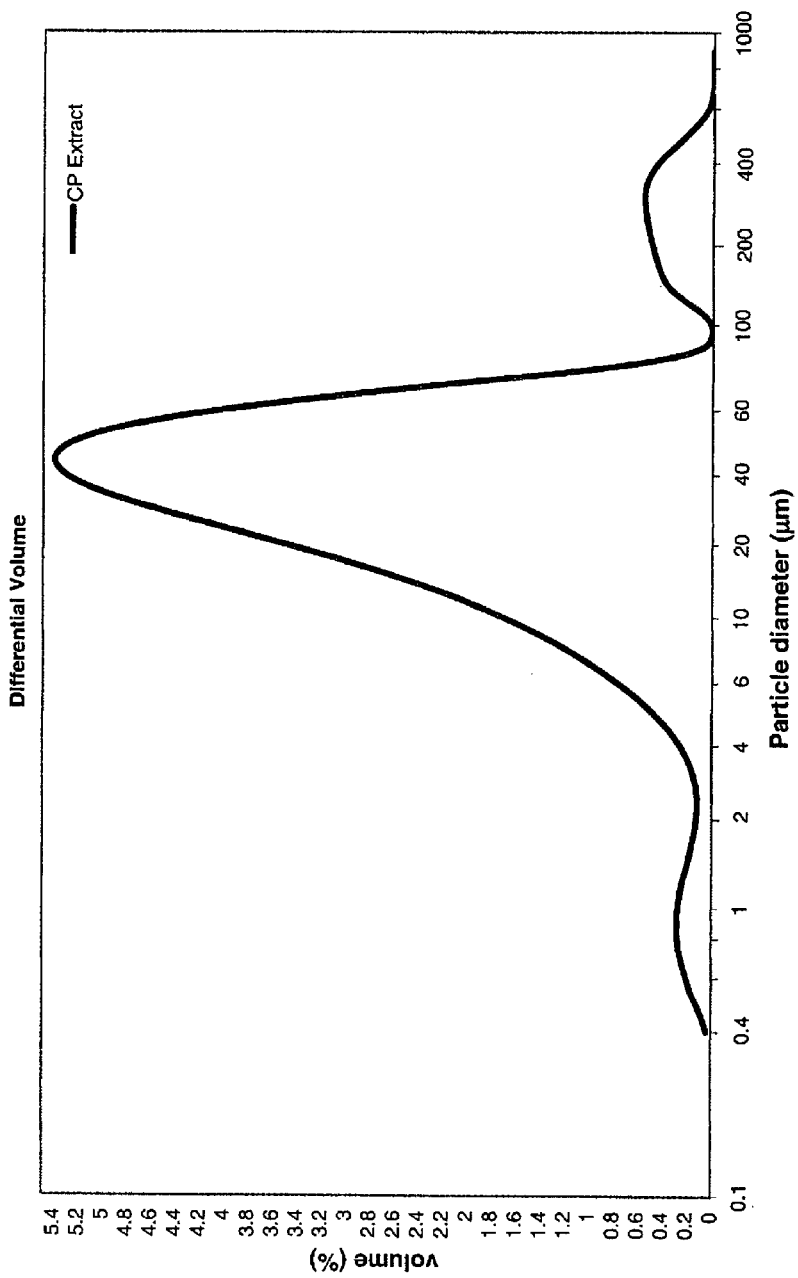
FIG. 1 shows the particle size distribution of an unmilled high CP cocoa extract.

Cocoa beans can be divided into four categories based on their color: predominantly brown (fully fermented), purple/brown, purple, and slaty (underfermented). Preferably, the cocoa solids are prepared from underfermented cocoa beans, i.e., slaty cocoa beans, purple cocoa beans, mixtures of slaty and purple cocoa beans, mixtures of purple and brown cocoa beans, or mixtures of slaty, purple, and brown cocoa beans. More preferably, the cocoa beans are slaty and/or purple cocoa beans which have higher cocoa polyphenol contents than fermented beans.

The term "fermentation factor" is a numerical quantification of the fermentation level of a batch of cocoa beans. Fermentation factors range from 100 (under/underfermented) to 400 (fully fermented). To assess the degree of fermentation, cocoa beans are typically subjected to a standard cut test for assessing quality as defined in industry grade standards. The bean halves are laid out on a board for visual inspection of color as well as defects which can arise during cocoa bean fermentation, drying, and/or storage.

The "fermentation factor" is a grading system for characterizing the fermentation of the cocoa beans. Slaty, being under/unfermented, is designated as 1, purple as 2, purple/brown as 3, and brown as 4. The percentage of beans falling within each category is multiplied by a weighted number. Thus, the "fermentation factor" for a sample of 100% brown beans would be 100×4 or 400, whereas the fermentation factor for a sample of 100% purple beans would be 100×2 or 200. A sample of 50% slaty beans and 50% purple beans would have a fermentation factor of 150 [(50×1)+(50×2)]. Cut tests applicable to cocoa beans derived from the Trinitario and Forastero type beans may or may not be applicable to cocoa beans derived from the Criollo type, for example where bean color variations ranging from fully purple to light tan can be encountered. Accordingly, the cut test based on color would not be applicable to specific cocoa genotypes lacking the anthocyanin pigments responsible for the purple color, such as Catango (or Catongo) type whose color is light tan. Other exceptions include "cocoa beans" derived from other *Theobroma* species and the *Herrania* species and their inter- and intra-specific crosses. The beans from these species are "tan" in color. For these types of beans the level of fermentation may be determined using a modified standard cut test.

Using the modified test, the surface of the halved bean is inspected for the degree of lines, fissures or cracks which form during fermentation, rather than the change of color. FIGS. 1(a)-(d) of the '913 patent illustrate the changes in the surface of the cut bean half during the fermentation. As can be seen from the figures, the number of lines/fissures and the extent to which they extend across the entire surface of the cut bean half increases as the bean is fermented. As the cocoa bean is fermeRts fermented, the surface develops small branch-like lines or fissures. This modified test can also be used to approximate the fermentation factor. A cocoa bean corresponding to FIG. 1(a) is designated as 100, FIG. 1(b) as 200, FIG. 1(c) as 300, and FIG. 1(d) as 400. While the definitions of the aforementioned categories are a general guide, assessment of the fermentation is well within the skill of the ordinary skilled artisan well versed in chocolate and cocoa processing (see pages 511-513 of Wood et al., Cocoa, $4^{th}$ Ed. (1985), incorporated herein by reference). The numerical indexes, 1-4 or 100-400, are qualitative terms that are used herein to reflect the relative fermentation of cocoa beans and therefore related to the relative concentration of cocoa polyphenols in cocoa beans. A value of 1 or 100 would reflect unfermented beans possessing the highest total amount or nearly the total amount of cocoa polyphenols. A value of 4 or 400 would reflect fully fermented beans possessing the amount of cocoa polyphenols remaining after fermentation. The actual cocoa polyphenol concentration of any cocoa bean sample or cocoa ingredient may be determined using the high performance liquid chromatographic (HPLC) technique described in U.S. Pat. No. 5,554,645 (Romanczyk et al.).

The term "fair average quality cocoa beans" refers to cocoa beans that have been separated from the pulp material and dried and are relatively free of mold and infestation. Such beans are a commercial commodity. The term includes any such bean that has been genetically modified or produced.

The term "raw freshly harvested cocoa beans" refers to seeds or beans freshly harvested from the cocoa pod and which have not been subjected to processing other than separation from the pulp. The term includes any such bean that has been genetically modified or produced.

Preparation of High CP Cocoa Extracts

The term "cocoa polyphenol" includes the flavan-3-ols (i.e., epicatechin and catechin) and procyanidin oligomers thereof which are present in cocoa beans and in some cocoa ingredients prepared from cocoa beans.

Cocoa extracts may be prepared by reducing cocoa beans to a powder, defatting the powder, and extracting and purifying the active compound(s) from the defatted powder. The powder is generally prepared by freeze-drying the cocoa beans and pulp, depulping and deshelling the freeze-dried beans, and grinding the deshelled beans or nibs. The extraction of the cocoa polyphenols is accomplished by solvent extraction techniques using aqueous alcohols such as methanol, ethanol, or isobutanol or aqueous ketones such as acetone. Acetates such as methyl acetate and ethyl acetate are used for extracting the monomers and lower oligomers. The extracts are purified by gel permeation chromatography, preparative high performance liquid chromatography (HPLC) techniques, or by a combination of such methods. See U.S. Pat. No. 5,554,645, the disclosure of which is incorporated herein by reference.

Cocoa extracts may also by prepared by solvent extracting high CP partially or fully defatted cocoa solids prepared from unfermented and/or underfermented cocoa beans or cocoa nibs. Preferably, the cocoa beans are only heated for a time at an internal bean temperature (IBT) sufficient to loosen the cocoa shells without roasting the cocoa nibs. See U.S. Pat. No. 6,015,913 and U.S. Pat. No. 6,312,753, the disclosures of which are incorporated herein by reference.

Extracts containing higher oligomers or containing monomers and lower oligomers can be prepared using the selective extraction procedure of U.S. Pat. No. 6,627,232, the disclosure of which is incorporated by reference. The process comprises the steps of (a) extracting the cocoa solids with ethyl acetate, (b) recovering the extracted cocoa solids, (c) extracting the recovered, extracted cocoa solids with acetone, ethanol, or mixtures thereof with up to 50 volume % water, and (d) separating the cocoa solids from the cocoa extract of step (c) to obtain an extract containing the higher oligomers. Optionally, the solvent is acidified to a pH of about 2 to about 4, e.g., with acetic acid. The '232 patent also provides a method for selectively extracting epicatechin, catechin, and lower molecular weight oligomers such as dimers and trimers using methyl or ethyl acetate.

The selective extraction of monomers and procyanidins oligomers from an aqueous mixture of cocoa polyphenols is disclosed in U.S. 2007-0078261-A, the disclosure of which is incorporated herein by reference. The process comprises extracting the aqueous mixture with n-butyl acetate and separating an aqueous phase enriched in procyanidin dimers and higher oligomers and a n-butyl acetate phase enriched in catechin and epicatechin. Subsequent extractions of the aqueous phases with various solvents or solvent mixtures provides aqueous and solvent phases enriched in various procyanidin oligomers.

Preparation of High CP Cocoa Solids and Chocolate Liquor

The term "cocoa ingredient" refers to a cocoa solids-containing material derived from shell-free cocoa solids (e.g., cake or powder), alkalized cocoa powder or alkalized chocolate liquor and the like. The term "chocolate liquor" refers to the dark brown fluid "liquor" formed by grinding a cocoa nib. The fluidity is due to the breakdown of the cell walls and the release of the cocoa butter during the processing which results in a suspension of ground particles of cocoa solids suspended in cocoa butter. The cocoa ingredients include those prepared from unfermented or underfermented beans because the beans have a higher cocoa polyphenol content.

Partially defatted cocoa solids having a high cocoa polyphenol (CP) content can be obtained by processing the cocoa beans directly to cocoa solids without a bean or a nib roasting step as disclosed in U.S. Pat. No. 6,015,913 (Kealey et al.). This method conserves the cocoa polyphenols because it omits the traditional roasting step. The method comprises the steps of: (a) heating the cocoa beans to an internal bean temperature just sufficient to reduce the moisture content to about 3% by weight and to loosen the cocoa shell; (b) winnowing the cocoa nibs from the cocoa shells; (c) pressing the cocoa nibs; and (d) recovering cocoa butter and partially defatted cocoa solids containing cocoa polyphenols.

Alternatively, a high CP chocolate liquor and/or high CP cocoa solids can be prepared by: (a) roasting selected cocoa beans having a fermentation factor of 275 or less to an internal bean temperature of 95° C. to 160° C.; (b) winnowing the cocoa nibs from the roasted cocoa beans; (c) milling the cocoa nibs into the chocolate liquor; and (d) optionally recovering cocoa butter and partially defatted cocoa solids from the chocolate liquor. Alternatively, the chocolate liquor and/or cocoa solids can be prepared by: (a) heating cocoa beans having a fermentation factor of 275 or less to an internal bean temperature of 95-135° C. to loosen the cocoa shell from the cocoa nibs; (b) winnowing the cocoa nibs from the cocoa shells; (c) roasting the cocoa nibs to an internal nib temperature of 95° C. to 160° C.; (d) milling the roasted nibs into a chocolate liquor; and (e) optionally recovering cocoa butter and partially defatted cocoa solids from the chocolate liquor.

Milling of Dried High CP Cocoa Extracts

The first embodiment relates to a high cocoa polyphenol (CP) cocoa extract which has been milled to reduce the particle size of the cocoa extract. The milled high CP cocoa extracts typically contain at least about 300 milligrams, preferably about 300 to about 700 milligrams, more preferably at least about 400 milligrams, even more preferably about 400 to about 600 milligrams, and most preferably about 400 to about 500 milligrams of total cocoa polyphenols per gram of the milled cocoa extract.

Milling can be carried out in any of the equipment which is typically used in dry milling powders. Air jet mills are particularly useful but hammer mills, cryogenic mills, or any other mills which significantly reduce the particle size without generating high temperatures for a long period of time are useful herein. As discussed above, cocoa polyphenols are lost when high temperatures are used in the preparation of cocoa ingredients such as the chocolate liquors, cocoa solids, and cocoa extracts. Useful air-jet-mills are described in U.S. Pat. No. 4,807,815 (Csillag et al.); U.S. Pat. No. 4,189,102 (Andrews); U.S. Pat. No. 3,559,895 (Fay); U.S. Pat. No. 4,056,233 (Fay); U.S. Pat. No. 4,504,017 (Andrews); U.S. Pat. No. 5,637,344 (Carpenter et al.); and U.S. Pat. No. 3,726,484 (Schurr), the disclosures of which are incorporated herein by reference.

Examples of useful commercially available jet pulverizers for producing air-jet milled powders include the TROST™ Air Impact Pulverizer, sold by Garlock Plastomer Products; the ROTO-JET sold by Fluid Energy Aljet, Inc. (Plumsteadville, Pa.); the MICRON MASTER® JET PULVERIZER sold by the Jet Pulverizer Company; AIR JET PULVERIZER sold by Nisshin Engineering Co., Ltd. (Buffalo Grove, Ill.), and the like.

Fat and/or Oil-Based Additives

An additive consisting essentially of a fat and/or an oil and optionally an emulsifier is useful for adding a dispersion of the milled high CP cocoa extracts to products such as foods, nutritional supplements, and pharmaceuticals.

The fat(s) and/or oil(s) act as carriers in additives containing the milled high CP cocoa extracts. There must be sufficient fat and/or oil to disperse the milled particles. Typically, the amount of fat or oil is about 35 to about 98% based on the total weight of the additive. Preferably, it is about 40 to about 70%, more preferably about 40 to about 60%, and most preferably about 45 to about 55%.

As used herein, the term "fat" refers to triglycerides used in food products, especially confectionery products such as chocolates. Useful fats include naturally occurring fats and oils such as cocoa butter, expeller cocoa butter, solvent-extracted cocoa butter, refined cocoa butter, milk fat, anhydrous milk fat, fractionated milk fat, milk fat replacers, butterfat, fractionated butterfat, and other vegetable fats, as well as other modifications of these fats, including cocoa butter equivalents (CBE), cocoa butter substitutes (CBS), cocoa butter replacers (CBR), anti-blooming agents such as behenoyl olecoyl behenate (BOB), reduced calorie fats and non-caloric fat substitutes. A reduced calorie fat is a fat having all the properties of a typical fat but having fewer calories than a typical fat. A non-caloric fat substitute, e.g., a sucrose polyester, likewise possesses all the typical fat characteristics, but is not absorbed after ingestion and thus is not metabolized.

Suitable oils include vegetable oil oils such as coconut oil, corn oil, sunflower oil, soybean oil, safflower oil, palm oil, peanut oil, sesame oil, cottonseed oil, olive oil, and like oils as well as fractionated or hydrogenated vegetable oils such as hydrogenated coconut oil, fractionated palm oil, and the like.

Syrup-Based Additives

Another embodiment of the invention relates to a syrup-based additive containing particles of the milled high CP cocoa extract dispersed therein. The additive consists essentially of (i) a syrup comprising water and a nutritive carbohydrate sweetener and/or a sugar substitute; (ii) the milled cocoa extract described above; and (iii) optionally one of the fats or oils discussed above. The syrup is present in an amount sufficient to allow the milled cocoa extract to be dispersed therein. Typically, the amount of syrup is about 35 to about 98% based on the total weight of the additive. Preferably it is about 40 to about 70%, more preferably about 40 to about 60%, and most preferably about 45 to about 55%. This syrup-based additive is useful in food bars such as granola bars and confectioneries such as chocolate chews.

Nutritive carbohydrate sweeteners, with varying degrees of sweetness intensity are useful herein. Preferably, the sweetener comprises a corn syrup or a blend of a corn syrup with another sweetener. Suitable sweeteners include those typically used in foods and include, but are not limited to, sucrose (e.g., from cane or beet), dextrose, fructose, lactose, maltose, glucose syrup or the solids thereof, corn syrup or the solids thereof, invert sugar, hydrolyzed lactose, honey, maple sugar, brown sugar, molasses and the like.

Sugar substitutes may be used to partially replace the sweetener in the syrup, particularly in the production of reduced-calorie products. The term "sugar substitute" includes high potency sweeteners, sugar alcohols (polyols), bulking agents, or combinations thereof. The high potency sweeteners include aspartame, cyclamates, saccharin, acesulfame, neo-hesperidin dihydrochalcone, sucralose, alitame, stevia sweeteners, glycyrrhizin, thaumatin, and mixtures thereof. The preferred high potency sweeteners include aspartame, cyclamates, saccharin, and acesulfame-K. Examples of sugar alcohols include those typically used in the art and include sorbitol, mannitol, xylitol, maltitol, isomalt, lactitol, and the like. The syrups may also contain bulking agents such as those typically used in combination with high potency sweeteners. The "bulking agents" may be any of those typically used and include polydextrose, cellulose and its derivatives, maltodextrin, gum arabic, and the like.

Preferably, the syrup comprises about 5% to 100% of corn syrup solids and up to 80% sugar, based on the total weight of the syrup. For the food bars, the corn syrup is about 5% to 100%, preferably about 65% to about 98%, and most preferably about 80% to about 95% and the sugar is up to about 20%, preferably about 1% to about 10%, and more preferably about 1% to about 5%. For a chocolate confectionery such as a chew, the corn syrup is about 5% to about 80%, preferably about 10% to about 50%, and most preferably about 20% to about 35%.

High CP Products

The products of the present invention are fat-based, oil-based, and/or syrup-based products which contain a milled cocoa extract having a total cocoa polyphenol content of at least about 300 milligrams, preferably about 300 to about 700 milligrams, more preferably about 400 to about 600 milligrams, and most preferably about 400 to about 500 milligrams per gram of the milled extract. The products have a reduced water availability. Such availability of water in a food is commonly termed "water activity". In general, a reduced water activity (under 0.91) indicates the existence of an environment in which most pathogenic bacteria will not generally grow, and 0.1-0.7 is preferred.

The products include foods, medical foods, food supplements, and pharmaceuticals. Suitable foods include those having a continuous fat phase such as confections; intermediate moisture, ambient, chilled or frozen dairy products; intermediate moisture, chilled or frozen fruit products and/or sugar products; aerated foods such as foams, dry powder coatings such as cocoa powder dustings for confectioneries; dry powder mixes for preparing sauces, condiments, salad dressings; and like products.

The products and additives of the present invention may contain other ingredients such as carbohydrates and/or sugar substitutes; milk solids; dry ingredients; proteins; natural and artificial flavors (e.g., spices, coffee, salt, and/or brown nutmeats, etc.); vitamins and minerals; sterols, stanols, and their esters; and L-arginine-containing ingredients such as nut pieces, nut flours, and nut pastes. Preferably, the foods are cocoa-containing foods, most preferably chocolate confectioneries.

As used herein, "food" is a material consisting of protein, carbohydrate and/or fat, which is used in the body of any organism to sustain growth, repair vital processes, and furnish energy. Foods may also contain supplementary substances such as minerals, vitamins, and condiments (Merriam-Webster Collegiate Dictionary, $10^{th}$ Edition, 1993).

As used herein, a "medical food" is a food that is prescribed by a doctor or a health care professional.

As used herein, "food supplement" is a product (other than tobacco) that is intended to supplement the diet that bears or contains one or more of the following dietary ingredients a vitamin, a mineral, an herb or other botanical, an amino acid, a dietary substance for use by man to supplement the diet by increasing the total daily intake, or a concentrate, metabolite, constituent, extract or combination of these ingredients (Merriam-Webster Collegiate Dictionary, $10^{th}$ Edition, 1993). When the term is used on food labels, "supplement" means that nutrients have been added in amounts greater than 50% above the U.S. Recommended Daily Allowance ("Understanding Normal and Clinical Nutrition", $3^{rd}$ Edition, Editors Whitney, Catalado, and Rolfes at page 525).

As used herein "pharmaceutical" is a medicinal drug (Merriam-Webster Collegiate Dictionary, $10^{th}$ Edition, 1993).

When dry, ready-to-eat foods such as granola bars are being prepared, the cocoa solids, particularly high CP cocoa solids, are pre-treated with sterol ester(s) and/or stanol ester(s) to prevent the loss of cocoa polyphenols. The amount can be about 9 to about 90% based on the weight of the cocoa solids. The sterol and/or stanol esters included in the products act as a cholesterol lowering agents. See U.S. 2005-0069625 A1 (Chimel et al.) published Mar. 31, 2005, the disclosure of which is incorporated herein by reference.

Emulsifying Agents

Emulsifying agents, also referred to as emulsifiers, may be used in the products or in the fat-based additives. Emulsifying agents are well known to play a critical role in suspension rheology and are used throughout food manufacturing, especially confectionery and chocolate manufacturing, to enhance the rheology (i.e., reduce viscosity and/or yield value) of solids suspensions. Soy lecithin is one of the oldest and most widely used emulsifying agents. In chocolate, lecithin demonstrates a significant viscosity lowering effect when used at an optimum concentration of about 0.3% to about 0.7% by weight of the finished chocolate.

Exemplary emulsifying agents include lecithin derived from vegetable sources such as soybean, safflower, corn, etc., fractionated lecithins, mono- and di-glycerides, di-acetyl tartaric acid esters of mono- and di-glycerides (also referred to as DATEM), monosodium phosphate derivatives of mono- and di-glycerides of edible fats or oils, sorbitan monostearate, polyoxyethylene sorbitan monostearate, hydroxylated lecithin, lactylated fatty acid esters of glycerol and propylene glycol, polyglycerol esters of fatty acids, propylene glycol mono- and di-glycerides of fats and fatty acids, and especially any emulsifying agents that may become approved for the U.S. Food and Drug Administration-defined soft candy category. It is considered within the skill of one in the art to select an emulsifying agent for use in the preparation of the products, Other emulsifying agents that may be used include polyglycerol polyricinoleate (PGPR), ammonium salts of phosphatidic acid (e.g., YN), sucrose esters, oat extracts, etc., and any emulsifying agent or combination thereof, found to be suitable in chocolate or similar fat/solid system. Selected combinations of emulsifying agents have been identified to provide reduced fat confectioneries. See U.S. Pat. No. 6,391,373 (Kaiser et al.) issued May 21, 2002, the disclosure of which is incorporated herein by reference. Combinations that are particularly useful for reduced fat confectioneries are combinations of lecithin, sucrose polyerucate sucrose polystearate, ammonium phosphatide, phosphated mono-di-glycerides/diacetyl tartaric acid of mono-glycerides (PMD/DATEM), or fractionated lecithin, with sucrose polyerucate and/or polyglycerol polyricinoleate. The combination of polyglycerol polyricinoleate, sucrose polyerucate, and soy lecithin, offers significant improvement in the rheology of reduced fat chocolates.

Carbohydrates

The term "carbohydrate" refers to nutritive carbohydrate sweeteners with varying degrees of sweetness intensity, They include, but are not limited to sucrose (e.g., from cane or beet), dextrose, fructose, lactose, maltose, glucose syrup solids, corn syrup solids, invert sugar, hydrolyzed lactose, honey, maple sugar, brown sugar, molasses, and the like. Sugar substitutes may be used to partially replace the nutritive carbohydrate sweeteners, particularly in the production of reduced-calorie confectioneries (e.g., chocolates). As used herein, the term "sugar substitute" includes high potency sweeteners, sugar alcohols (polyols), and/or bulking agents. The high potency sweeteners include aspartame, cyclamates, saccharin, acesulfame, neo-hesperidin, dihydrochalcone, sucralose, alitame, stevia sweeteners, glycyrrhizin, and/or thaumatin. The preferred high potency sweeteners include aspartame, cyclamates, saccharin, and acesulfame-K. Examples of sugar alcohols include sorbitol, mannitol, xylitol, maltitol, isomalt, lactitol, and the like. The products may also contain bulking agents such as those typically used in combination with high potency sweeteners. The term "bulking agents" includes any of those typically used in the art such as polydextrose, cellulose and its derivatives, malodextrin, gum arabic, and the like.

Flavoring Agent

The term "flavoring agent" refers to compound(s) or composition(s) used in edible products and confectioneries such as chocolate to impart a desired taste and/or aroma. Exemplary flavoring agents include vanillin, spices, and naturally expressed citrus or spice oils.

Chocolate

The term "chocolate" is intended to refer to all chocolate or chocolate-like compositions with a fat-based component phase or fat-like composition. The term is intended, for example, to include standardized and non-standardized chocolates, i.e., including chocolates with compositions conforming to the U.S. Standards of Identity (SOI) and compositions not conforming to U.S. Standards of Identity (non-SOI), respectively, including dark chocolate, baking chocolate, milk chocolate, sweet chocolate, mixed dairy product chocolate, low fat chocolate, white chocolate, aerated chocolates, compound coatings, non-standardized chocolates, and chocolate-like compositions, unless specified otherwise.

In the United States chocolate is subject to a standard of identity established by the U.S. Food and Drug Administration (FDA) under the Food, Drug and Cosmetic Act. Definitions and standards for the various types of chocolate are well established in the U.S. Non-standardized chocolates are those chocolates which have compositions which fall outside the specified ranges of the standardized chocolates. Chocolates also include those containing crumb solids or solids fully or partially made by a crumb process.

Non-standardized chocolates result when, for example, the nutritive carbohydrate sweetener is replaced partially or completely; or when the cocoa butter, cocoa butter alternative, cocoa butter equivalent, cocoa butter extender, cocoa butter replacer, cocoa butter substitute or milk fat are replaced partially or completely; or when components that have flavors that imitate milk, butter or chocolate are added or other additions or deletions in the formula are made outside the FDA Standards of Identity for chocolate or combinations thereof. Chocolate-like compositions are those fat-based compositions that can be used as substitutes for chocolate in applications such as panning, molding, or enrobing, for example, carob.

Chocolate may take the form of solid pieces of chocolate, such as bars or novelty shapes, and may also be incorporated as an ingredient in other, more complex confections where chocolate is combined with and generally coats other foods such as caramel, peanut butter, nougat, fruit pieces, nuts, wafers, ice cream, or the like. These foods are characterized as microbiologically shelf-stable at 65°-89° F. (19-29° C.), under normal atmospheric conditions.

Ready-to-Eat Food Bars

Any suitable grain, flour, and/or protein can be used in ready-to-eat food bars containing high CP cocoa ingredients. Typical grains include flaked oats, wheat, barley, rye, toasted rolled oats, crisped rice, and the like. Typical flours include bran, corn, wheat, and rice. Typical proteins include soy, whey, milk, peanut, and egg proteins. Optional dry ingredients include chopped or whole nuts, such as almonds, hazelnuts, peanuts, and coconut flakes, and dried fruits such as blueberries and cherries. The syrup comprises about 30% to about 75%, preferably about 40% to about 65%, more preferably about 50% to about 60%, and most preferably 55% by weight of the bar. Preferably, a granola bar with or without fruit and/or nut inclusions is enrobed or decorated with chocolate, preferably a tempered dark chocolate, yogurt, or flavored granulated sugars. If desired, the granola bar can contain supplemental dietary fiber(s) which are added in the form of compressed flakes. As used herein, the term "supplemental dietary fiber" refers to dietary fibers which are added to the bar apart from the fiber which is typically included in a granola bar. The supplementary dietary fibers can be of various types and preferably are a mixture of various types, more preferably a mixture of soluble and insoluble dietary fibers. Sources generally known to contribute insoluble fiber include, but are not limited to, soy fiber, apple fiber, corn bran, wheat bran, oat bran, barley bran, rye bran, triticale bran, cellulose, pea fiber, sugar beet fiber, and peanut fiber. Sources generally known to contribute soluble fiber include, but are not limited to, gum arabic, gum ghatti, guar gum, pectins, psyllium, carrageenans, xanthan, tragocanth, karaya, locust bean gum, agar, and alginates.

Non-Cocoa Polyphenols

The products herein may contain polyphenols from sources other than cocoa. These include the polyphenols found in various nuts, fruits, vegetables, and botanicals. Suitable nuts include peanuts, walnuts, almonds, hazelnuts, soy beans, and the like. Nut pieces, nut skins, nut pastes, and/or nut flours are also useful herein. Peanut skins contain about 17% procyanidins and almond skins contain up to about 30% procyanidins. Nut skins can be used, e.g., in the nougats used in confectioneries. The skins of apples and oranges also contain polyphenols. Grape seeds and pomegranates are also high in polyphenols.

L-Arginine

Products and additives containing the milled high CP cocoa extracts may also contain L-arginine to stimulate nitric oxide production. See U.S. Pat. No. 6,805,883 (Chevaux et al.) issued Oct. 19, 2004, which discloses sources for L-arginine. The disclosure of the '883 patent is incorporated herein by reference.

Phytosterols

The fat-, oil-, or syrup-based products may also contain sterols, stanols, and/or their esters as cholesterol-lowering agents. Stanols are saturated derivatives of sterols in which all carbon-carbon bonds in the rings are saturated. Stanols typically have 28 or 29 carbon atoms and include beta-sitostanol, clionastanol, 22,23-dyhydrobrassicastanol and campestenol. Stanols are found in small amounts in nature but may be easily prepared from sterols by hydrogenating sterols by any of the several methods known to those skilled in the art. When a sterol starting material is prepared from a plant material, it will contain a mixture of several different sterols thus, after hydrogenation, the resulting stanol will also be a mixture of different stanols. Cocoa oil extracted from cocoa hulls is a good source of phytosterols. Cocoa phytosterols are a mixture of free and bound sterols, with the free sterols being up to about 90% of the phytosterols present. The phytosterols include campesterol, β-sitosterol, stigmasterol, cycloartenoyl, 24-methylene cycloartenoyl, as well as minor amounts of other phytosterols. The bound phytosterols include the fatty acid esters or ferulate derivatives of the phytosterols.

Esterified forms of sterols and stanols are the forms most useful herein. Esterification renders the sterols/stanols more soluble in fats and oils, for example, sterols may be esterified with fatty acid esters such as rapeseed oil, canola oil, and like oils. Suitable fatty acids include saturated or unsaturated fatty acids typically having 14 to 24 carbon atoms. Examples of esterified sterols include sitosterol acetate, sitosterol oleate, and stigmasterol oleate. Stanol esters may be prepared, as is known in the art, for example as described in U.S. Pat. No. 6,174,560, U.S. Pat. No. 6,031,118, U.S. Pat. No. 5,958,913, U.S. Pat. No. 5,892,068, and U.S. Pat. No. 5,502,045, the disclosures of which are incorporated herein by reference. The '045 patent describes the interesterification of free stanols with a methyl ester mixture of $C_2$ to $C_{22}$ fatty acids (e.g., rapeseed oil) using an interesterification catalyst such as sodium ethylate. An interesterification process such as that disclosed in the '045 patent can also be used to esterify sterol esters. In another embodiment, useful stanol esters are prepared by esterifying at least one sterol with a $C_2$ to $C_{22}$ fatty acid ester as described in the '913 patent cited above.

Particularly useful are canola oil sterol esters, sunflower oil sterol esters, and their mixtures. These sterol ester mixtures melt at around 30°-50° C.; however, typically the esters are heated to about 60°-80° C. to ensure the entire mixture is liquified. To conserve cocoa polyphenols the liquid or liquefied sterol/stanol esters are mixed with high CP cocoa solids to protect the CPs during further processing of the cocoa solids into the final products.

Analytical and Testing Procedures

High Performance Liquid Chromatography (HPLC) Procedures

In Examples 6-10, the separation of the cocoa polyphenols, which include the flavan-3-ols epicatechin and catechin as well as the procyanidin oligomers, was performed on an Agilent 1100 Series HPLC system equipped with an autosampler, quaternary pump, column heater, photodiode array and fluorescence detector. The quantitative work was performed on the Develosil diol 100 A (250×4.6 mm, 5μ particle size) purchased from Phenomenex (Torrance, Calif.). The chromatographic mobile phase was a binary gradient (solvents A and B) which consisted of acidic acetonitrile ((A), $CH_3CN$:HOAc, 98:2; v,v) and acidic aqueous methanol ((B), $CH_3OH$: $H_2O$:HOAc, 95:3:2; v,v,v). The starting mobile phase conditions were 7% B which was held isocratic for 3 minutes. Subsequently, solvent B was ramped to 37.6 over 57 minutes and to 100% B 3 minutes thereafter. The conditions were held at 100% B for 7 minutes prior to returning to starting conditions (7% B) over 6 minutes. Baseline resolution for flavanols (DP=1) and procyanidins (DP=2-10) was achieved with a total run time of 76 minutes. The UV detection was set to 280 nm. Fluorescence detection was conducted with an excitation wavelength of 230 nm and emission at 321 nm. Other FLD conditions included a photomultiplier tube gradient. In order to have all components (DP=1-10) in ranges that were within the detection range of FLD. A photomultiplier tube gain gradient was employed. The gain was changed according to time at different time intervals. The photomultiplier tube gain was set to 7 from 0-8 minute(s), set to 9 from 8.1-15.0 minutes, and finally set to 10 from 15.1-76 minutes. Precise gain gradient time settings need to be assessed for individual columns—small column to column shifts in retention time must be considered. The column temperature was held at 35° C. The flow rate was 1 mL/min and typical injection volume was 5 μL. A cyano (CN) (4×3.0 mm) SecurityGuard cartridge was obtained from Phenomenex (Torrance, Calif.) and employed to protect the column. The guard column was installed with a SecurityGuard Guard Cartridge Kit (also obtained from Phenomenex). The autosampler was set to and held at 5° C.

In the other examples where total cocoa polyphenols were determined, a slightly different analytical method was used to determine the total cocoa polyphenol content of the high CP cocoa extracts. This method is based upon work reported in Hammerstone, et al. "Identification of Procyanidins in Cocoa (*Theobroma cacao*) and Chocolate Using High-Performance Liquid Chromatography/Mass Spectrometry", J. Ag. Food Chem. 47 (10):490-496 (1999). The utility of this analytical method was applied in a qualitative study of a broad range of food and beverage samples reported to contain various types of proanthocyanidins, as reported in Lazarus et al., "High-performance Liquid Chromatography/Mass Spectrometry Analysis of Proanthocyanidins in Foods and Beverages", J. Ag. Food Chem. 47 (9):3693-3701 (1999). The analysis of Lazarus et al. uses fluorescence detection because of higher selectivity and sensitivity.

In both methods, composite standard stock solutions and calibration curves are generated for each procyanidin oligomer through the decamer, or in some cases through the dodecamer, using the analytical method reported in Adamson et al., "HPLC Method for the Quantification of Procyanidins in Cocoa and Chocolate Samples and Correlation to Total Antioxidant Capacity", J. Ag. Food Chem. 47 (10):4184-4188 (1999). Samples were then compared with the composite standard to accurately determine the levels of cocoa polyphenols.

Particle Size Analysis

Particle size may be measured by any of several techniques known in the art. The mean particle size of a distribution is defined as a mean volume particle diameter over a given distribution, measured using the Coulter® laser light scattering technique. The largest and smallest particle size in a given distribution may be determined by scanning electron microscope (SEM) laser light scattering or the like. Individual powders were analyzed by laser light scattering using a Coutler LS230 particle size analyzer (sold by Coulter Corporation, Hialeah, Fla.).

Measurement of Bitterness and Astringency

The bitterness and astringency of the milk chocolate products are measured using an art-recognized, standardized testing protocol: Descriptive Analysis using the Spectrum Method intensity scale, as detailed in the $2^{nd}$ Edition of Sensory Evaluation Techniques by M. Meilgaard et al. (CRC Press). The selection and training of the 10-20 panelists was carried out as detailed starting at page 142. The panel was specifically focused on confectionery products (e.g., hard candy, caramel, nougat, candy bars, toffee). The intensity scale (0 to 15) for tastes and chemical feelings is described at page 173 (see Schedule B).

The definitions used by the trained panelists are as follows. "Bitter" is defined as the taste on the tongue stimulated by substances such as quinine, caffeine, and hop bitters. "Astringent" is defined as the shrinking or puckering of the tongue surface caused by substances such as tannins or alum.

The examples which follow are intended as an illustration of certain preferred embodiments of the invention, and no limitation of the invention is implied.

EXAMPLES

Example 1

Cocoa Bean Source and Method of Preparation

Harvested cocoa pods were opened and the beans with pulp were removed for freeze drying. The pulp was manually removed from the freeze-dried mass. The unfermented freeze-dried cocoa beans were manually dehulled and ground to a find powdery mass with a TEKMAR Mill. The resultant mass was then defatted overnight by Soxhlet extraction using distilled hexane as the solvent. Residual solvent was removed from the defatted mass by vacuum at ambient temperature.

Example 2

Extraction of Cocoa Polyphenols from Defatted Cocoa Mass

Cocoa polyphenols were extracted using a modification of the method described by Jalal and Collin (1977). Fifty gram batches of the defatted cocoa mass from Example 1 were extracted twice with 400 mL of 70% acetone/deionized water and extracted twice with 400 mL of dichloromethane ($CHCl_3$). The solvent phase was discarded. The aqueous phase was then extracted four times with 500 mL of ethyl acetate. Any resultant emulsions were broken by centrifugation on a Sorvall RC 28S centrifuge operated at 2,000×g for 30 minutes at 10° C. To the combined ethyl acetate extracts, 100 to 200 mL deionized water were added. The solvent was removed by evaporation at 45° C. with a rotary evaporator held under partial vacuum. The resultant aqueous phase was frozen in liquid nitrogen ($N_2$) followed by freeze drying on a LABCONCO Freeze Dry System.

Example 3

Preparation of High CP Partially Defatted Cocoa Solids

Commercially available cocoa beans having an initial moisture content of about 7 to 8% by weight were pre-cleaned in a scalperator. The pre-cleaned beans were further cleaned in an air fluidized bed density separator. The cleaned beans were then passed through an infra-red heating apparatus. The depth of the beans in the vibrating bed of the apparatus was about 2-3 beans deep. The surface temperature of the apparatus was set at about 165° C., thereby producing an internal bean temperature (IBT) of about 135° C. in a time ranging from 1 to 1.5 minutes. This treatment caused the shells to dry rapidly and separate from the cocoa nibs. The broken pieces separated by the vibrating screen were reintroduced into the product stream prior to the winnowing step. The resulting beans after micronizing should have a moisture content of about 3.9% by weight. The beans emerged at an IBT of about 135° C. and were immediately cooled to about 90° C. in about 3 minutes to minimize additional moisture loss. The beans were then winnowed to crack the beans, to loosen the shells, and to separate the lighter shells from the nibs while at the same time minimizing the amount of nib lost with the shell reject stream. The resulting cocoa nibs were screw pressed to extract the cocoa butter from the cocoa solids.

A sample of cocoa solids, produced according to the above-described process from unfermented cocoa beans (fermentation factor 233), when analyzed according to the Adamson et al. method discussed above, typically will have a total cocoa procyanidin content of about 50 to about 75, preferably about 60 to about 75, or more preferably about 75 to about 80 milligrams of total cocoa polyphenols per gram of defatted cocoa solids. Example 4—Preparation of High CP Cocoa Extracts from High CP Partially Defatted Cocoa Solids.

Example 4

Preparation of High CP Cocoa Extracts from High CP Partially Defatted Cocoa Solids The cocoa solids from Example 3 were contacted at room temperature for from 0.5 to 3.5 hours with an aqueous organic solvent. The solvent was about 75% ethanol/25% water (v/v) or about 80% acetone/20% water (v/v). The micella was separated from the cocoa residue and concentrated by evaporation to a 30 to 50% total solids content. The concentrated extract was then spray-dried.

Example 5

Preparation of High CP Chocolate Liquor

Fair average quality (FAQ) Sulawesi cocoa beans having an initial moisture content of 7.4% by weight and a fermentation factor level of 233 (31% slaty, 29% purple, 22% purple brown, and 17% brown) were selected as the starting material. The cocoa beans were passed through a vibrating infrared heating apparatus (manufactured by Micronizer Company Ltd., U.K.). The feed rate of the beans through the infra-red heater bed angle controls the heat treatment the beans receive. The amount of time the beans spend in the infra-red heater (residence time) is determined by the bed angle and the feed rate. At the outlet of the micronizer the IBT of the beans was measured. The surface temperature of the beans exiting the infra-red heater is higher than the IBT. Rapid surface cooling brings the surface temperature close to the IBT in less than 1 minute. The beans were further processed into chocolate liquor using lab scale liquor processing equipment. The cracked beans were passed through a laboratory scale winnowing system to separate the shells and the nibs. The cocoa nibs were then milled into a coarse liquor in a Melange (Pascall Engineering Co., Ltd. Of England). The normal operating temperature for the liquor in the Melange was approximately 50° C. The cocoa nibs were ground in the Melange for 1 hour.

The total cocoa polyphenol content was measured using the Adamson et al. method described above. When heated at an IBT of 107° C. for 42 seconds, the total cocoa polyphenol content of the defatted chocolate liquor was 39,690 micrograms. At 126° C. IBT and 82 seconds residence time, it was 28,815 micrograms, and at 148° C. IBT and 156 seconds residence time it was 23,937 micrograms.

Example 6

Preparation of Milled High CP Cocoa Extracts

Spray-dried cocoa extracts, prepared as in Example 4, were milled using an air jet mill (Fluid Energy Aljet Roto-Jet). The extracts were hand fed into the mill where 110 psi grinding air was used. Classifier speeds of 5,000 and 10,000 rpm were used to separate the finely milled extract.

Representative samples were analyzed in a Beckman Coulter Particle Size Analyzer.

FIG. 1 shows the particle size distribution of the unmilled, spray-dried extract. The mean particle size and median particle size of the unmilled extract were 45.4 microns and 28.83 microns, respectively. 90 Volume % of the particles were less than 64.9 microns ($D_{90}$), 75 volume % of the particles were less than 44.86 microns ($D_{75}$), 50 volume % of the particles were less than 28.83 microns ($D_{50}$), 25 volume % of the particles were less than 16.34 microns ($D_{25}$), and 10 volume % of the particles were less than 8.112 microns ($D_{10}$). The total cocoa polyphenol content of the unmilled extract was 468.5 milligrams per gram of the unmilled extract.

Figure 2:
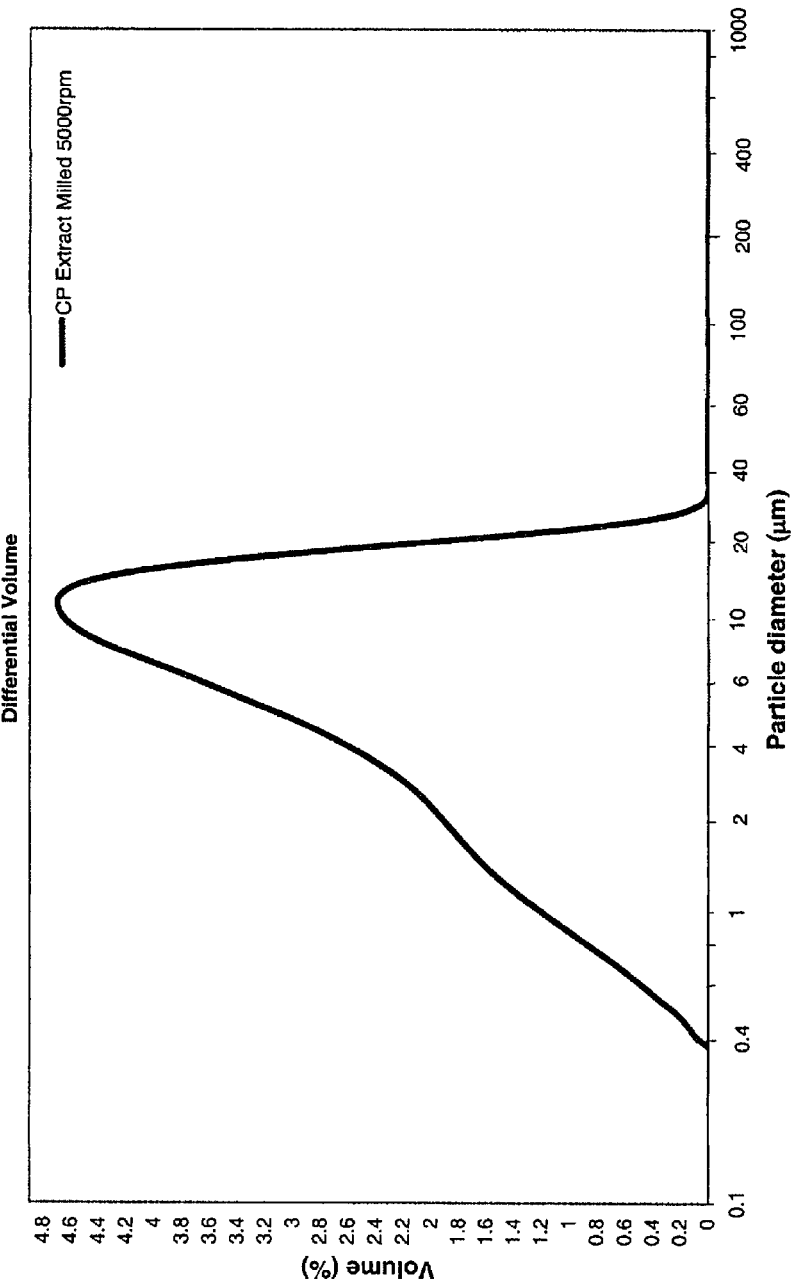
FIG. 2 shows the particle size distribution of a high CP cocoa extract air jet milled with a classifier speed of 5,000 rpm.

FIG. 2 shows the particle size distribution of the spray-dried cocoa extract air jet milled using a classifier speed of 5,000 rpm. The mean particle size and median particle size of the milled extract were 7.49 microns and 6.517 microns, respectively. Ninety (90) volume % of the particles were less than 15.26 microns ($D_{90}$), 75 volume % of the particles were less than 11.21 microns ($D_{75}$), 50 volume % of the particles were less than 6.517 microns ($D_{50}$), 25 volume % of the particles were less than 2.889 microns (D25), and 10 volume % of the particles were less than 1.35 microns ($D_{10}$). The total cocoa polyphenol content of the milled extract was 477.9 milligrams per gram of the milled extract.

Figure 3:
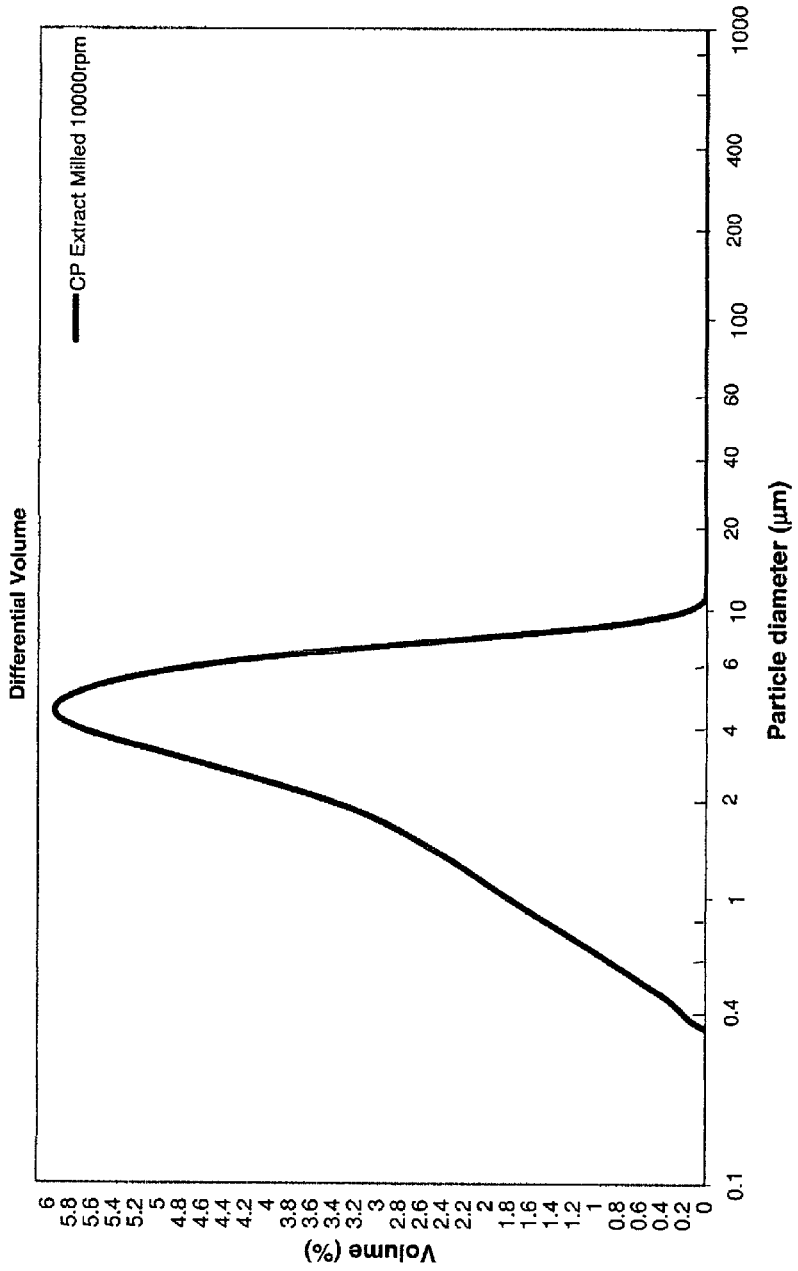
FIG. 3 shows the particle size distribution of a high CP cocoa extract air jet milled with a classifier speed of 10,000 rpm.

FIG. 3 shows the particle size distribution of the spray-dried cocoa extract air jet milled using a classifier speed of 10,000 rpm. The mean particle size and median particle size of the milled extract were 3.71 microns and 3.452 microns, respectively. Ninety (90) volume % of the particles were less than 6.755 microns ($D_{90}$), 75 volume % of the particles were less than 5.192 microns ($D_{75}$), 50 volume % of the particles were less than 3.452 microns ($D_{50}$), 25 volume % of the particles were less than 1.913 microns ($D_{25}$), and 10 volume % of the particles were less than 1.057 microns ($D_{10}$). This milled extract had a total cocoa polyphenol content of 515.3 mg/g. The differences between the total cocoa polyphenol content of the unmilled and milled extracts are not significant and within the differences typically seen for these analyses.

Figure 4:
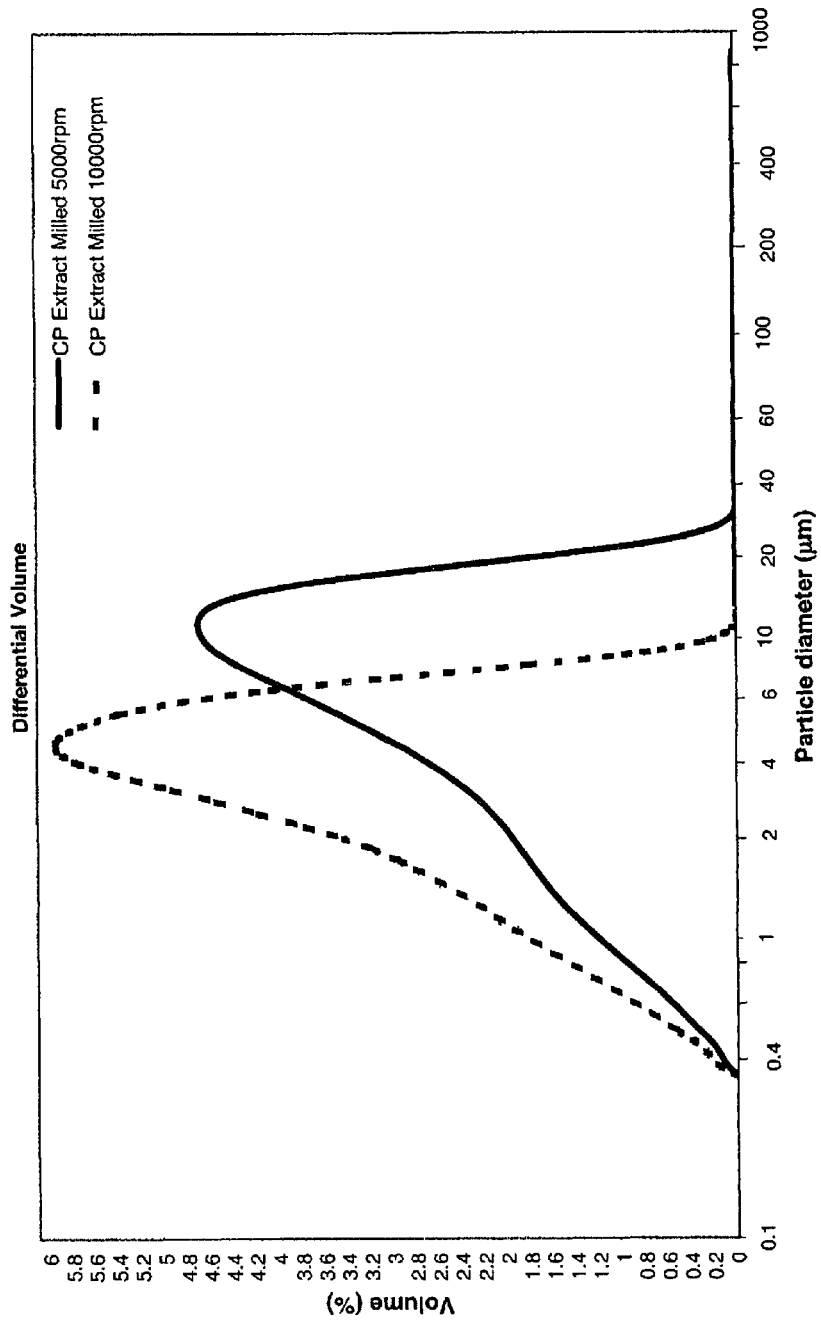
FIG. 4 is an overlay of the milled high CP extracts of FIGS. 2 and 3.

FIG. 4 is an overlay of the milled high CP cocoa extracts of FIGS. 2 and 3.

Example 7

Dispersing High CP Cocoa Extracts in Cocoa Butter

An unmilled high CP cocoa extract having a mean particle size of about 45 microns and a high CP cocoa extract milled to mean particle size 3.71 microns were dispersed in cocoa butter warmed at 40° C. The mixtures contained 1.5 wt. % of the cocoa extract and 98.5 wt. % of the cocoa butter. When tasted, the cocoa butter containing the milled high CP cocoa extract was found to be significantly less bitter and astringent than the cocoa butter containing the unmilled high CP cocoa extract.

Example 8

Dispersing High CP Cocoa Extracts in Anhydrous Milk Fat

An unmilled high CP cocoa extract having a mean particle size of about 45 microns and a high CP cocoa extract milled to a mean particle size of 3.71 microns were dispersed into anhydrous milk fat warmed at 40° C. The mixtures contained 1.5 wt. % of the high CP cocoa extracts and 98.5 wt. % of the anhydrous milk fat. When tasted, the anhydrous milk fat containing the milled high CP cocoa extract was found to be significantly less bitter and astringent than the anhydrous milk fat containing the unmilled high CP cocoa extract.

Example 9

Dispersing High CP Cocoa Extracts in Corn Syrup

An unmilled high CP cocoa extract having a mean particle size of about 45 microns and a high CP cocoa extract milled to a mean particle size of 3.71 microns were dispersed into 63 DE corn syrup warmed at 40° C. The mixtures contained 1.5 wt. % of the high CP cocoa extracts and 98.5 wt. % of the corn syrup. When tasted, the corn syrup containing the milled high CP cocoa extract was found to be significantly less bitter and astringent than the corn syrup containing the unmilled high CP cocoa extract.

Example 10

Dispersing High CP Cocoa Extracts in Milk Chocolates

An unmilled high CP cocoa extract having a mean particle size of about 45 microns and a milled high CP cocoa extract (mean particle size of about 3.7 microns) were dispersed into milk chocolates which had been warmed at 40° C. The high CP chocolate mixtures contained 1.03 wt. % of the high CP cocoa extracts and 98.97 wt. % of the milk chocolate. The high CP milk chocolates were tempered separately and moulded into 8 gram solid chocolate pieces.

The bitterness and astringency of the milk chocolates were evaluated by a trained sensory panel who rated the chocolates on a scale of 1 to 15 using the procedure previously described. A total of 150 milligrams of cocoa polyphenols in a 40 gram serving were consumed by each panelist. The chocolate pieces were 8 grams each and 5 pieces were consumed in each serving. Milk chocolate containing no cocoa extract was included for comparison.

The test milk chocolate containing the milled high CP extract (mean particle size of about 3.7 microns) was significantly less bitter and astringent than the control milk chocolate containing the unmilled high CP cocoa extract (mean particle size of about 45 microns). The test milk chocolate containing the milled high CP cocoa extract had a les displeasing aftertaste than the control milk chocolate containing the unmilled high CP cocoa extract.

The comparative chocolate was a milk chocolate containing no high CP cocoa extract, the test chocolate was a milk chocolate containing a milled high CP cocoa extract having a mean particle size of about 3.7 microns, and the control chocolate was a milk chocolate containing the same amount of an unmilled high CP cocoa extract having a mean particle size of about 45 microns.

Figure 9:
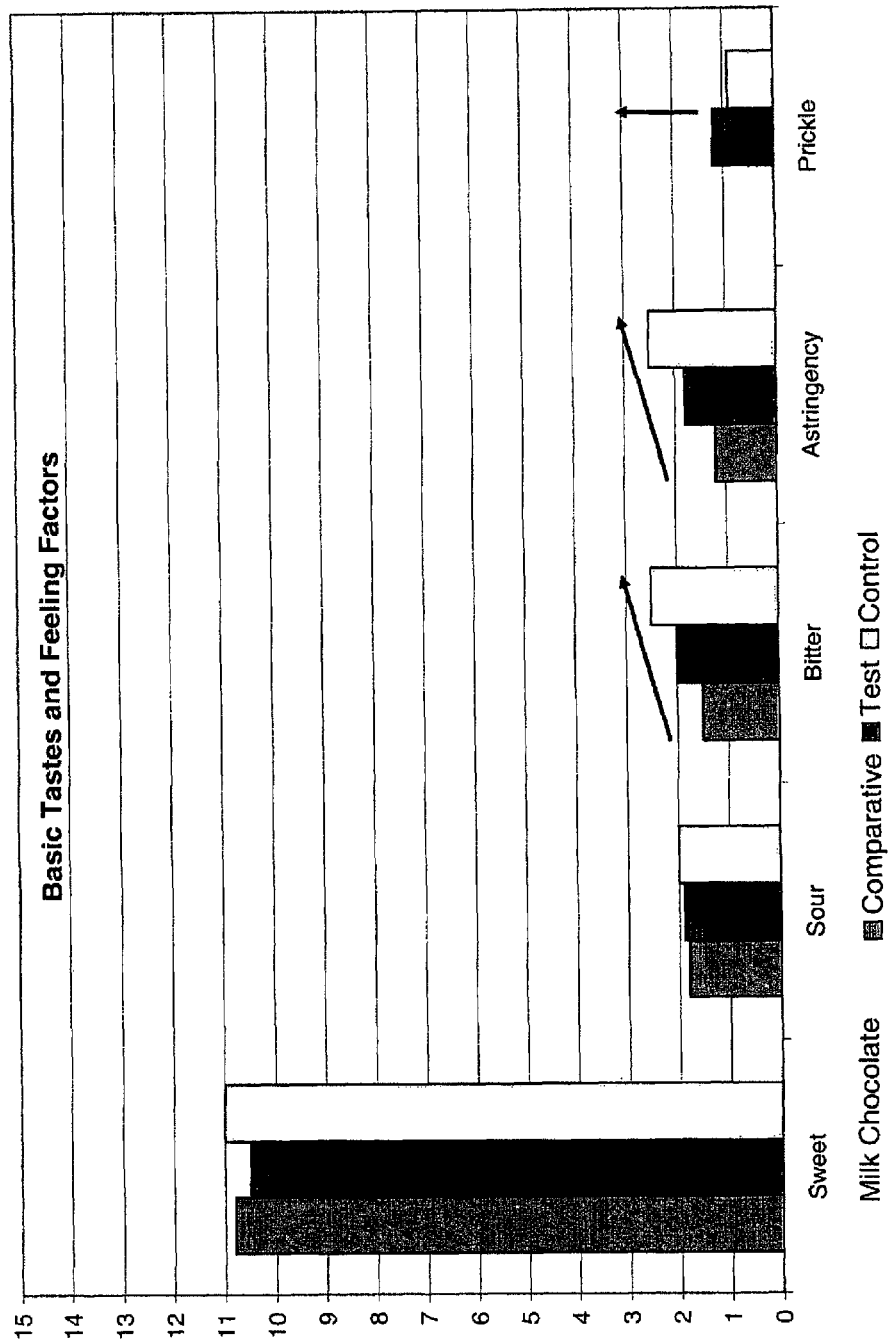
FIG. 9 compares the basic taste factors for a milk chocolate containing no high CP cocoa extract (comparative milk chocolate), a milk chocolate containing an unmilled cocoa extract having a mean particle size of about 45 microns (control milk chocolate), and a milk chocolate containing a milled cocoa extract having a particle size of about 3.7 microns (test milk chocolate).

The impact of adding cocoa extracts to milk chocolates are shown in FIG. 9.

Example 11

Reducing the Particle Size of High CP Partially Defatted Cocoa Cake (Comparative Example)

This example shows that milling a high CP, partially defatted cocoa cake does not reduce the bitter/astringent flavor and results in a product showing a significant loss of total cocoa polyphenols.

The unmilled cocoa cake had a total cocoa polyphenol content of about 72 milligrams per gram of the defatted cake. The particle size of the cocoa cake was reduced by milling at varying speeds in an air classifier mill (ACM). The air flow and the feed rate were kept constant throughout the milling process. The classifier and rotor speeds were varied to achieve the desired particle size distribution. The milling results are shown below.

Particle Size Analysis and Corresponding ACM Conditions:

| No. | Micro meters ($\mu$m) | $d_{90}$ ($\mu$m) | Mean Diameter ($\mu$m) | Classifier Speed (rpm) | Rotor Speed (rpm) | Air Flow Rate (SCFM) | Feed Rate (kg/hr) |
|---|---|---|---|---|---|---|---|
| 1 | 13.75 | 27.61 | 13.50 | 3400 | 7000 | 500 | 35 |
| 2 | 23.75 | 36.02 | 16.82 | 3400 | 6500 | 500 | 35 |
| 3 | 49.44 | 51.19 | 22.11 | 3000 | 5000 | 500 | 35 |
| 4 | 81.00 | 87.16 | 36.61 | 2000 | 5000 | 500 | 35 |

The total cocoa polyphenol content was determined using the method of Hammerstone et al. discussed above. The unmilled cocoa cake contained 71.45 milligrams of total cocoa polyphenols per gram of the defatted cake. Sample No 4, milled to a particle size of 81.00 microns, had a total cocoa polyphenol content of 72.56 milligrams per gram of the defatted powder. Sample No. 1, milled to a mean particle size of 13.50 microns, had a total cocoa polyphenol content of only 50.80 milligrams per gram of the defatted powder. Thus, the total cocoa polyphenol content of the finely ground sample was reduced from 71.45 to 50.80 mg/g. More significantly, the milled products showed no flavor improvement. There were no significant differences in the bitterness/astringency and the grittiness/chalkiness when the milled products were evaluated in chocolate chews.

Example 12

Grinding High CP Cocoa Extract (Comparative Example)

This example demonstrates that grinding, rather than dry milling, a high CP cocoa extract did not reduce the particle size of the spray-died, high CP cocoa extract. The blender used for the grinding was a 10 speed Osterizer Blend Master® (Model 50200 MP) which is the same type of liquid blender used in Example 12 of U.S. Pat. No. 6,312,753 (Kealey et al.). The blender used in Example 12 was a Hamilton Beach Blendmaster liquid blender (Model #50100, Type B12).

A spray-dried cocoa extract having a mean particle diameter of about 26 microns, where about 90% of the particles were less than about 82 microns, was ground in the Osterizer blender at high speed for 1 minute and for 6 minutes. A total of 300 grams of the spray-dried cocoa extract was placed in the 5 cup glass container of the Osterizer blender (which was thus filled to the 1¾ mark). The blender was set on liquefy and the sample was ground for 1 minute and then for 6 minutes. The powder was stirred between the grindings. Representative samples were analyzed using the Beckman Coulter Particle Size Analyzer.

Figure 5:
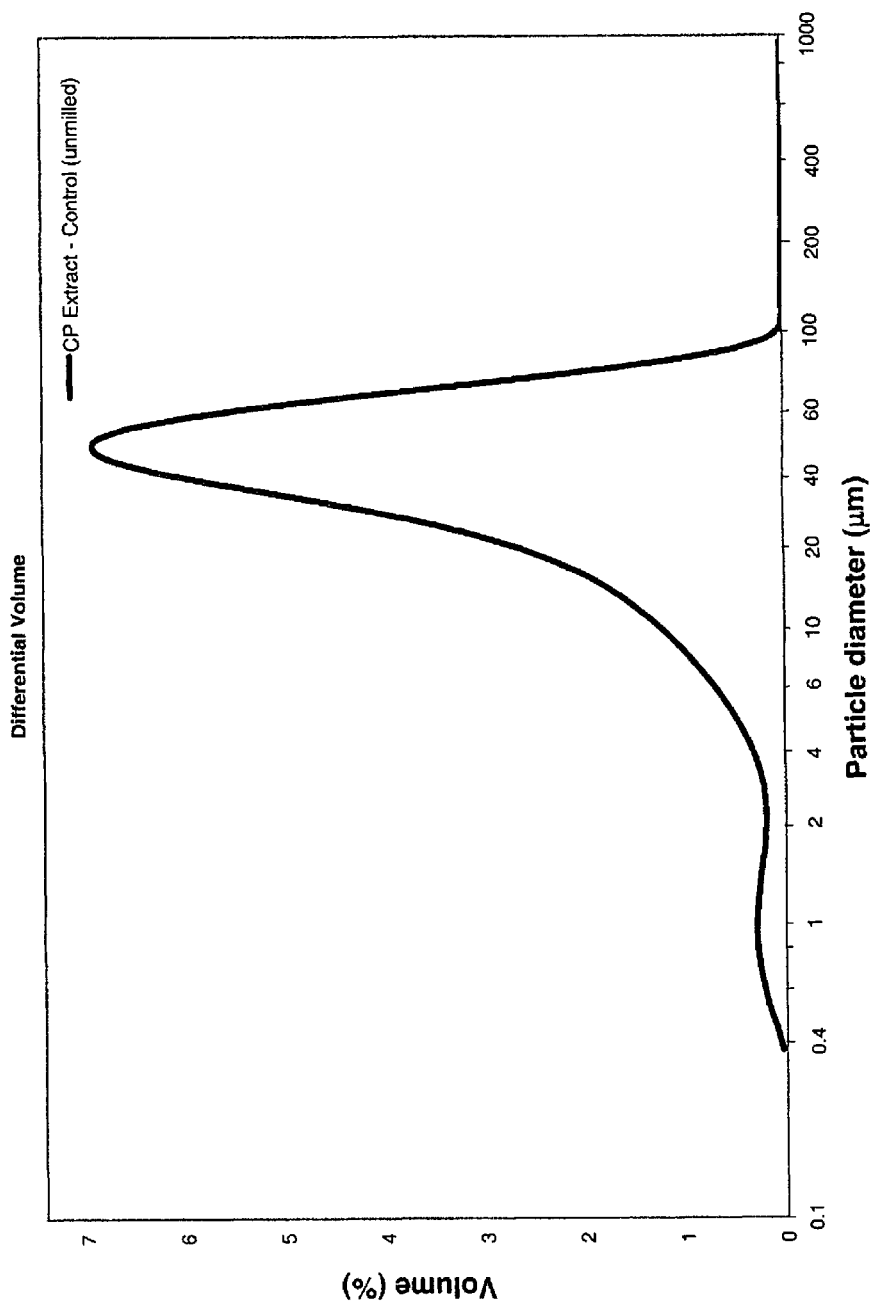
FIG. 5 shows the particle size distribution of an unmilled high CP cocoa extract.
Figure 6:
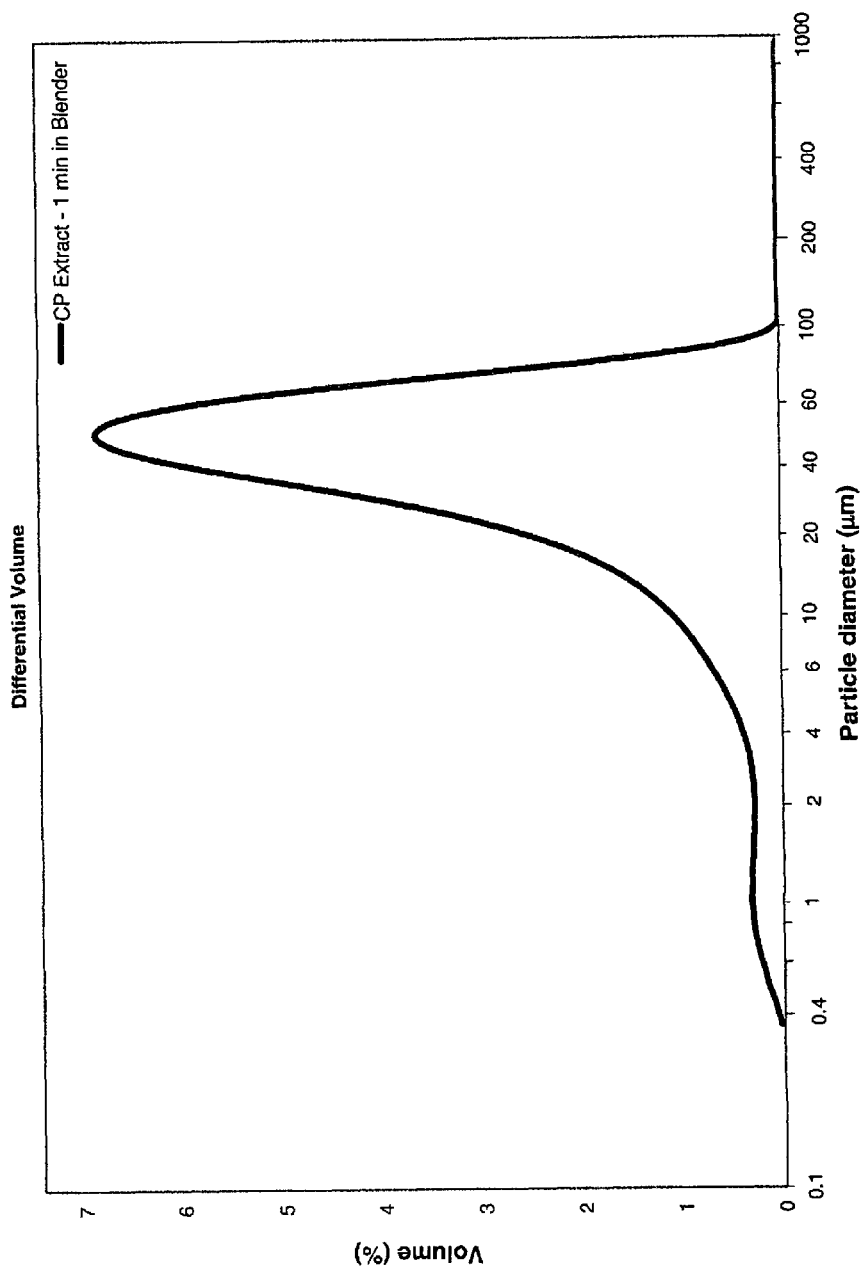
FIG. 6 shows the particle size distribution of a high CP cocoa extract ground for 1 minute at high speed in an Osterizer blender.
Figure 7:
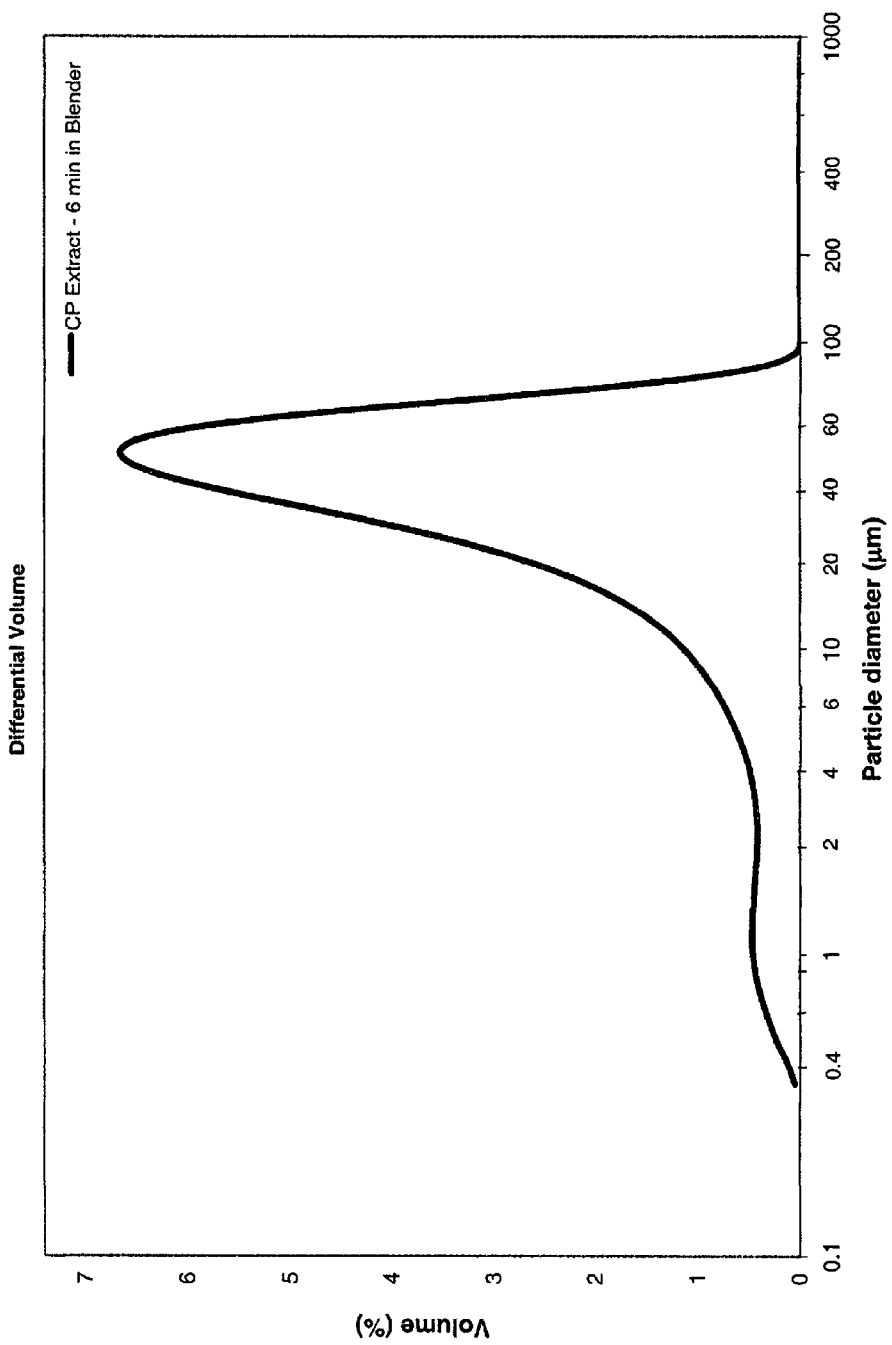
FIG. 7 shows the particle size distribution of the high CP cocoa extract ground for an additional 5 minutes at high speed in the Osterizer blender.
Figure 8:
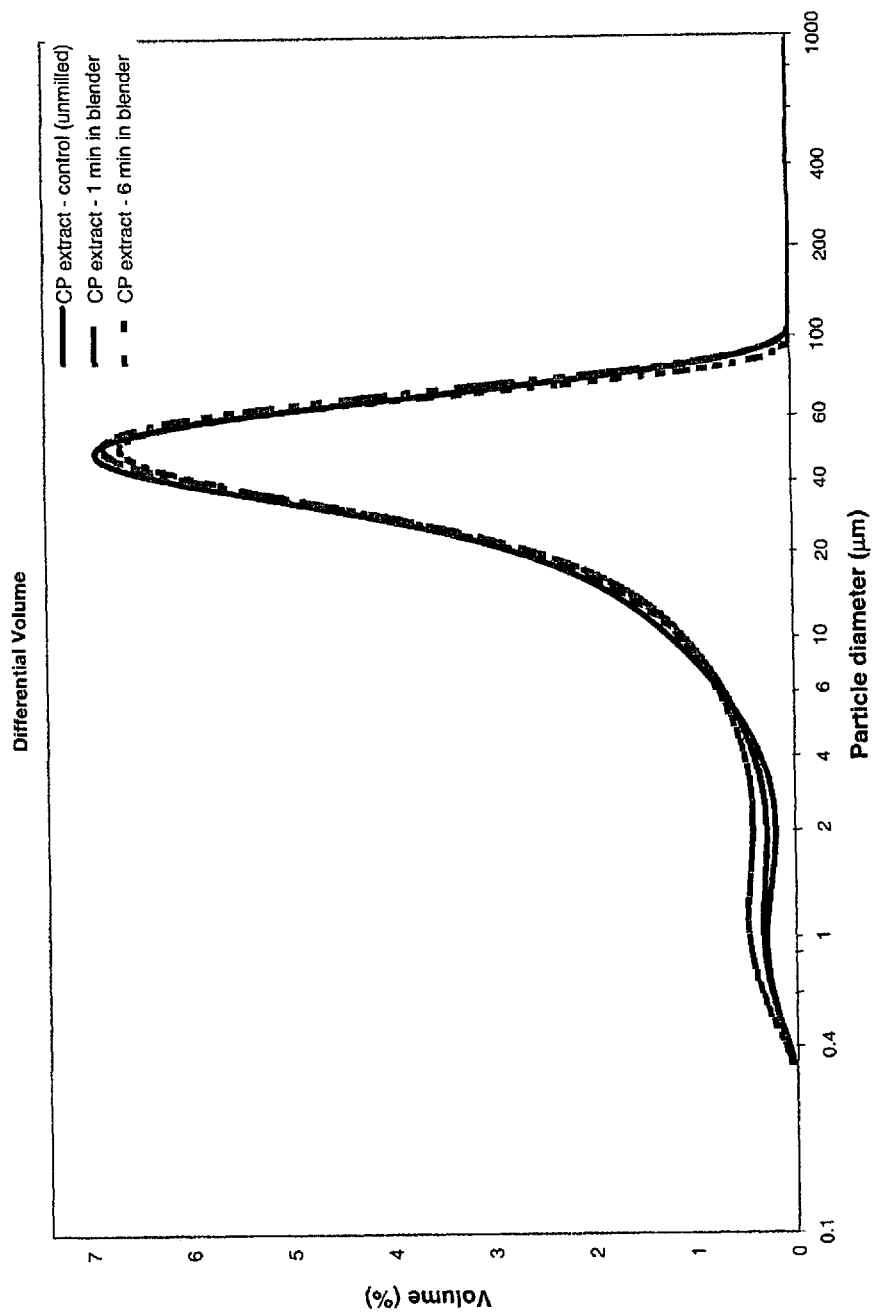
FIG. 8 is an overlay of the particle size distribution of the milled high CP extracts of FIGS. 5 and 6 on the unmilled high CP extract of FIG. 4.

The ground, spray-fried cocoa extract had almost the same particle size distribution as the non-ground, spray-dried cocoa extract. See FIG. 5 which shows the particle size distribution of the non-ground, spray-dried cocoa extract and FIGS. 6 and 7 which show the particle size distribution of spray-dried cocoa extracts ground for 1 minute and then for an additional 5 minutes (6 minutes total). FIG. 8 is an overlay of the particle distribution for the ground cocoa extracts and the unground cocoa extract which demonstrates that there was no particle size reduction.

Example 13

Cereal Product with High CP Cocoa Powder and Milled High CP Cocoa Extract

A cereal is made according to the following formulation:

| Ingredient | % |
| --- | --- |
| Soft Wheat Flour | 37.09 |
| Hard Wheat Flour | 16.64 |
| Sugar, Granulated | 30.33 |
| Sodium Bicarbonate | 0.19 |
| Monocalcium Phosphate | 0.19 |
| Glycerol Monostearate | 0.43 |
| Salt | 1.73 |
| Cocoa Powder | 12.02 |
| Milled High CP Cocoa Extract | 1.30 |
| Total | 100.00 |

All of the ingredients except the cocoa powder and cocoa extract are combined in a small ribbon blender and blended for 3 minutes. At the end of the blending cycle, all of materials are pneumatically conveyed to an AccuRate Feeder at 40 kg/hr, along with the cocoa powder and the milled high CP cocoa extract, which is fed through the K-tron Feeder at 6.18 kg/hr, into a Werner-Pfleiderer Twin Screw Extruder (Model ZSK57 with Bullet Tips). Water is added at a rate of 1.2 l/hr. The extruder is started up using standard operating procedures. Feed rates for the dry blend and the water are adjusted to targets. The screw RPM is set to 200. The cocoa feeder is adjusted to target and the cereal tubs are collected. Empty cereal tubes are fed through the crimper and collected in 2 foot lengths. Separate pillows are made by snapping at crimped edges.

Example 14

Cooked Vanilla Pudding made with High CP Cocoa Extract

| Ingredient | % |
| --- | --- |
| JELL-O Vanilla Pudding Mix | 95.00 |
| Milled High CP Cocoa Extract | 5.00 |
| Total | 100.00 |

The pudding is cooked by adding 5% cocoa extract to the dry pudding mix and blending using a wire whip. Two cups of whole milk are added to the pudding mixture in a Magna Lite saucepan. The dry mixture and milk are cooked and stirred constantly using a wire whip over medium heat on a HOT-POINT stove (Model RS744G0N1BG) until the mixture comes to a full boil. The pudding is removed from the heat, poured into a storage container, and stored in the refrigerator.

Example 15

Brownies with Milled High CP Cocoa Extract

Brownies are made using a high CP cocoa extract according to the following formulation:

| Ingredient | % |
| --- | --- |
| Shortening | 11.90 |
| Chocolate Liquor | 8.40 |
| Milled High CP Cocoa Extract | 1.7 |
| Sugar | 37.60 |
| All Purpose Flower | 23.49 |
| Baking Powder | 0.14 |
| Salt | 0.14 |
| Eggs | 16.60 |
| Vanilla | 0.13 |
| Total | 100.00 |

The cocoa ingredients and shortening are placed in a Kitchen Aid K45 bowl. The bowl is then placed on top of a MAGNA Lite Saucepan (4¼.5 qt.), which has 345 grams of boiling (100° C.) water in it. This double boiler is then heated on a HOTPOINT stove over low heat. When the mixture is melted, it is removed from the heat. The sugar, eggs, and vanilla are mixed into the melted mixture. The remaining dry ingredients are mixed in and the dough is spread onto a greased 13"×9"×2" baking pan. The brownies are baked at 350° F. in a HOTPOINT oven for about 30 minutes until the brownies pull away from the sides of the pan.

Example 16

Chocolate Cookies made with High CP Cocoa Extract

Chocolate cookies are made using the ingredients shown below:

| Ingredient | % |
| --- | --- |
| Soft Butter | 30.50 |
| Confectioner's Sugar | 7.60 |
| Unsifted Flour | 45.80 |
| Cocoa Powder | 13.46 |
| Milled High CP Cocoa Extract | 1.84 |
| Water | 0.35 |
| Vanilla Extract | 0.45 |
| Total | 100.00 |

The oven is pre-heated to 325° F. The butter and one-fourth of the sugar are creamed in a Kitchen Aid mixer for about 2 minutes. The remaining ingredients are added and mixed for about 3 minutes. The dough is shaped into small balls, put on an ungreased cookie sheet, and baked at 325° F. for 15-17 minutes.

Example 17

Rice and Cheese Sauce Mix with Milled High CP Cocoa Extract

A mix is prepared using the following formulation:

| Ingredient | % |
| --- | --- |
| Seasoning Mix w/Cheese | 22.00 |
| Dried Vegetables | 3.00 |
| Dry Rice | 71.00 |
| Milled High CP Cocoa Extract | 4.00 |
| Total | 100.00 |

The ingredients are combined in a sauce pan with 2¼ cups of water and 1 to 2 tablespoons of butter. The mixture is brought to a boil and then allowed to simmer for about 10 minutes until most of the water is absorbed. The mix is then allowed to stand for about 5 minutes to allow the cheese sauce to thicken.

Example 18

Extruded Energy Bar Prepared with Milled High CP Cocoa Extract

The bars are prepared using the following formulation:

| Ingredient | % |
| --- | --- |
| Carbohydrate Syrup | 20-30 |
| Fruit/Fruit Preparation | 10-15 |
| Protein Powder (milk or soy origin) | 5-20 |
| Micronutrients | 4-5 |
| Simple Sugars | 10-20 |
| Maltodextrin | 10-15 |
| Crisp Rice/Rice | 10-13 |
| Cocoa Powder | 8-12 |
| Milled High CP Cocoa Extract | 1-3 |
| Fat | 2-5 |
| Flavor | 0.1-0.5 |
| Total | 100.00 |

The ingredients are mixed in a JH Day 50 gallon jacketed stainless steel double arm sigma blade mixer set to 50° C. The carbohydrate syrup, fat, and fruit/fruit preparation are combined in the mixer and mixed at 50 rpm until homogenous (about 5 minutes). With the mixer running, the remaining ingredients are gradually added in the following order and blended until homogenous: micronutrients, flavor, cocoa ingredients, simple sugars, maltodextrin, protein powder, and crisp rice/rice. The resulting mass is transferred to the hopper of a jacketed extruder maintained at 40° C. to keep the mass soft and pliable for forming. The mass is extruded through the nozzle block onto a conveyor belt that transfers the strips through a cooling tunnel. A guillotine is used to cut the bars exiting the cooling tunnel at 15-20° C.

Example 19

Hard Candy Made with Milled High CP Cocoa Extract

Formed and deposited types of hard candy are prepared using the formulation below by the methods described in Lees & Jackson, $1^{st}$ Edition, Sugar Confectionery and Chocolate Manufacture, pages 176-186 (1995).

| Ingredient | % |
| --- | --- |
| Sugar | 42.85 |
| High Maltose Corn Syrup | 38.09 |
| Water | 12.19 |
| Buffered Lactic Acid | 1.90 |
| Flavoring | 0.19 |
| Coloring | 0.0057 |
| Cocoa Powder | 1.32 |
| Milled High CP Cocoa Extract | 3.45 |
| Total | 100.00 |

Example 20

Fruit and Gelatin Pastry Bar made with Milled High CP Cocoa Extract

A strawberry fruit filling is made using the following formulation:

| Ingredient | Wet wt % | Amount (g) |
| --- | --- | --- |
| Xanthan gum extra fine | 1.0 | 5.0 |
| Hydrogenated soybean oil | 1.25 | 6.25 |
| Water | 10.0 | 50.0 |
| Glycerin USP or food grade Corn syrup solids | 7.0 | 35.0 |
| Maltrin M250 (78% solids with 61.9 g water) | 56.23 | 281.2 |
| Low moisture apple flake powder | 5.0 | 25.0 |
| Natural strawberry flavor | 2.0 | 10.0 |
| Strawberry puree concentrate | 12.0 | 60.0 |
| Malic acid, fine granular | 0.5 | 2.5 |
| Red #40 strawberry color | 0.02 | 0.1 |
| Milled High CP Cocoa Extract | 5.0 | 25.0 |
| Total | 100 | 500.00 |

For making the fruit filling, the gum is hydrated in cold water using a blender. The corn syrup solids, water, fruit puree, and glycerin are cooked on a stove top to a temperature of 230° F. using medium to high heat to a temperature of 230° F. The mixture is removed from the heat and allowed to cool. Hydrated gum is added to the mixture and the mixture is heated to 216° F. The mixture is again removed from the heat and allowed to cool for at least 5 minutes. The high CP cocoa extract, acid, color, apple powder and melted fat are added to the mixture. The mixture is allowed to cool for and additional 2 minutes. Flavor is added to the mixture with thorough mixing.

The pastry wrapper is made according to the following formulation:

| Ingredient | Wet wt % | Amount (g) |
| --- | --- | --- |
| Blended flour | 36.5 | 182.5 |
| 30% hard flour (54.75 g) | | |
| 70% soft flour (127.75 g) | | |
| Brown sugar roasted oats | 14.6 | 73.0 |
| Wheat bran | 7.3 | 36.5 |
| Gum arabic (Acacia FCC) | 0.6 | 3.0 |
| Kelco gum (Kelite CM) | 0.6 | 3.0 |
| Soy lecithin | 0.8 | 4.0 |
| Sodium bicarbonate | 0.6 | 3.0 |
| Sodium acid pyrophosphate | 0.4 | 2.0 |
| Brown sugar, granulated | 6.3 | 31.5 |
| Hydrogenated soybean oil | 5.2 | 26.0 |
| Water | 21.22 | 106.1 |
| Flour salt | 1.0 | 5.0 |
| Glycerin USP or food grade | 4.1 | 20.5 |
| Kelco GFS, prehydrated | 0.78 | 3.9 |
| Total | 100.00 | 100.00 |

For making the pastry wrapper, the gum arabic, Kelite CM, sodium bicarbonate, sodium acid pyrophosphate, salt, Kelco GFS, and glycerin are hydrated in water using a blender. Lecithin is stirred into the melted fat. The remaining dry ingredients are added to a mixing bowl. The fat blend is added to the dry ingredients using a Kitchen Aid mixer on speed 2. The gum blend is slowly added into the mixing howl. After mixing, the dough is allowed to stand for 15 minutes while covered with a wet paper towel to decrease the stickiness. A Rondo Sheeter is used to achieve a dough thickness of 2.5 mm. The dough is cut into 4"×4" squares weighing 33 g.

Using a pastry bag, 19.5 g of the fruit filling is applied to the top of each dough square. The dough is folded over to make a bar and the ends of the bar are sealed shut with crimping. Using a knife, holes are poked into the top of the bar to help heat escape and to prevent bar explosion. The bars are baked for 6½ minutes at 357° F. The weight of the final baked bar should be 45.5 g.

Example 21

Sugar Tablets with High CP Cocoa Extract

Wet process tablets are made according to the following formulation:

| Ingredient | Wet Cocoa Tablet | Final Cocoa Tablet After Drying (Dry wt. basis) |
|---|---|---|
| Sucrose-6X | 41.30 | 51.19 |
| Cocoa Powder | 25.89 | 31.68 |
| Milled High CP Cocoa Extract | 8.50 | 10.40 |
| Water | 21.66 | 4.50 |
| Gum Arabic | 1.26 | 1.41 |
| Gelatin 200 | 0.62 | 0.73 |
| Bloom Vanilla 4X | 0.76 | 0.09 |
| Total | 100.00 | 100.00 |

The gelatin is soaked in water and the sucrose is premixed with the cocoa ingredients. After the gelatin is hydrated, it is heated to 90° C. and gum arabic is added with high shear. This solution, with flavor, is mixed into ¼ of the sucrose/cocoa mixture, and the remaining sucrose/cocoa mixture is slowly added while mixing (in a Hobart or Kitchen Aid Ultra Power mixer). The formulation is mixed for 10-15 minutes and slabbed to the desired thickness (~5 mm). After drying and punching out in the desired shape (discs), the pieces are dried further to a final moisture of approximately 3-6%.

Example 22

Granola Bars with A High CP Fudge Topping

A fudge formulation using a milled high CP cocoa extract is made according to the following recipe:

| Ingredient | % |
|---|---|
| Powdered sugar (6X) | 27.4 |
| High Fructose Corn Syrup (55%) | 20.0 |
| Partially Hydrogenated Soybean Oil (6034) | 10.75 |
| Lactose (Alpha Mono) | 9.25 |
| Powdered Lactose (Alpha Mono) | 11.0 |
| Cocoa Powder | 8.3 |
| Milled High CP Cocoa Extract | 1.7 |
| Glycerin | 2.0 |
| Non-Fat Dry Milk (Low-Heat) | 5.0 |
| Water | 2.0 |
| Calcium Carbonate | 1.35 |
| Soy Lecithin | 0.5 |
| Salt | 0.25 |
| Vanilla | 0.5 |
| Total | 100.00 |

For making the fudge topping, the dry ingredients are blended in a Kitchen Aid mixer on low speed for approximately 3-4 minutes or until well blended. The hydrogenated soybean oil is melted in a microwave oven at 55-64° C. The soy lecithin is dispersed in the melted oil. The oil/lecithin mixture is poured into the blended dry ingredients in a Hobart mixer running on slow speed. The speed of the mixer is gradually increased and the water, glycerin, and high fructose corn syrup are added. The resulting fudge topping is mixed for 2-3 minutes or until thoroughly blended.

The finished bars are made according to the following formulations:

Granola Recipe

| Ingredient | % |
|---|---|
| Crisp Rice | 30.2 |
| Mini Wheat Flakes | 33.7 |
| Brown Sugar Oats | 36.1 |
| Total | 100.00 |

Finished Product Profile:

| Ingredient | % |
|---|---|
| Chocolate | 37.0 |
| Granola/Rice | 21.0 |
| Binder | 21.0 |
| Fudge | 21.0 |
| Total | 100.00 |

The finished product is made by blending the granola ingredients with the binder and slabbing onto wax paper with a rolling pin to about 15 mm high. The fudge topping is slabbed onto the granola base and allowed to set for about an hour. The bars are cut to the following dimensions:

| Height | 15 mm |
|---|---|
| Width | 25 mm |
| Length | 84 mm |

Cut bars are then enrobed in the high CP chocolate.

Example 23

High CP Milk Chocolate with High CP Cinnamon Caramel

A milk chocolate is hand tempered at 86° F. and then used to make shells in various shaped molds. About 965 grams of standard caramel is warmed to 55° C. and 20 grams of milled high CP cocoa extract and 15 grams of cinnamon are added to the warmed caramel and mixed well. The caramel is allowed to cool and is then pastry bagged into chocolate shells. The shells are then bottomed with tempered chocolate and removed from the molds. The molded piece should consist of 6 grams of milk chocolate and 4 grams of caramel.

Finished Product:

| Ingredient | Usage Level % |
|---|---|
| Milk Chocolate | 60.0 |
| High CP Caramel | 40.0 |
| Total | 100.00 |

Example 24

High CP Dark Chocolate with Chocolate-Flavored Nougat

The chocolate is hand tempered at 86° F.-88° F. and used to make shells in various shaped molds. The formula for chocolate-flavored nougat is used to make frappe A total of 5 grams of milled high CP cocoa extract is added to 104 grams of slurry which is folded into the frappe at a ratio of 92.40% frappe to 7.60% slurry. The finished chocolate-flavored nougat is then slabbed onto the cooling table and cut to fit the molded shells. The shells are then bottomed with tempered chocolate and removed from the molds. The molded piece consists of 22.5 grams of dark chocolate and 12.5 grams of chocolate-flavored nougat.

| Ingredient | Usage Level | # of Samples |
| --- | --- | --- |
| Chocolate-Flavored Nougat | 84.89 | 20 |
| Dark Chocolate | 15.00 | |
| Milled High CP Cocoa Extract | 0.11 | |
| Total | 100.00 | |

Example 25

Chocolates Containing Milled Cocoa Extract and Peanuts

A 10 lb Sigma blade mixer is used to mix together ingredients within the concentration ranges set forth below.

| Ingredient | % Concentration (by weight) |
| --- | --- |
| Sucrose | 40.00 |
| Chocolate Liquor | 54.00 |
| Milled High CP Cocoa Extract | 2.00 |
| Fat | 3.50 |
| Lecithin | 0.50 |
| Total | 100.00 |

The lecithin and fat are combined and mixed using a 10 lb. Sigma blade mixer until homogenous. The resulting fat/lecithin mixture is added to the granulated sucrose in a second 10 lb. Sigma mixer. The sucrose, fat, and lecithin are mixed at about 35° C. to about 90° C. until homogeneous. The remaining ingredients, including the chocolate liquor and milled high CP cocoa extract are added and mixed until homogeneous. The resulting mixture is refined to a micrometer particle size of about 20 microns, conched, and standardized. Peanuts in an amount of approximately 5-30 percent by weight of the final product are added to form a product high in cocoa polyphenols and L-arginine.

Example 26

Peanut Butter Food Products

Pre-roasted peanuts are ground with salt and sugar as desired for forming peanut butter. While mixing, a cocoa powder and a milled high CP cocoa extract are added to the mixture in amounts of about 2 to 3% and 0.5 to 3% weight of the total mixture. The product contains cocoa polyphenols and L-arginine.

Example 27

Dark Chocolate Containing Peanuts

A dark chocolate is prepared using the following general recipe:

| Ingredient | Range (wt. 5) |
| --- | --- |
| Sucrose | 15-35 |
| Chocolate Liquor | 40-75 |
| Cocoa Powder | 1-10 |
| Milled High CP Cocoa Extract | 0.5-3 |
| Fat | 1-10 |
| Vanillin | 0.1-0.5 |
| Lecithin | 0.1-1.0 |
| Total | 100.00 |

Peanuts in an amount of approximately 5 to 30 percent by weight of the total product are added.

Example 28

Dry Drink Mix Containing High CP Cocoa Extract and L-Arginine

A dry drink mix containing cocoa powder, a high CP cocoa extract, and L-arginine is made using the following formulation:

| Ingredient | % |
| --- | --- |
| Sugar | 59 |
| Skim Milk Powder | 20 |
| Malt Powder | 1.9 |
| Cocoa Powder | 5.0 |
| Milled High CP Cocoa Extract | 3.0 |
| Peanut Flour | 10.0 |
| Vanillin | <0.01 |
| Lecithin | <0.995 |
| Salt | <0.1 |
| Flavoring | <0.1 |
| Total | 100.00 |

The dry ingredients are batched according to the above formulation and mixed for one hour in a Kitchen Aid Professional Mixer using a wire whip at #2 speed. The lecithin is agglomerated prior to use in a Niro-Aeromatic Agglomerator.

Example 29

High CP Chocolate Chews Containing Sterol Esters

The chews are prepared from the ingredients shown below by pre-mixing the sterol esters, cocoa solids, milled high CP cocoa extract, lecithin, and dark chocolate liquor or milk chocolate liquor, for example in a Z-blade mixer. The mixture is incorporated into a cooked syrup (heated to 66° C.) containing the remaining ingredients. The moisture content of the syrup is about 9%. The mixture is slowly cooled, rolled, and wrapped. The moisture content of the final mixture should be about 8.3-8.7%.

Dark Chocolate Chew:

| Ingredient | % Formula |
| --- | --- |
| Corn Syrup (63 D.E.) | 27.000 |
| Sugar (Cane or Beet) | 21.000 |
| Sweetened Condensed Skim Milk | 15.000 |
| Dark Chocolate Liquor | 20.000 |
| Cocoa Powder (10-12% fat) | 6.500 |
| Milled High CP Cocoa Extract | 1.500 |
| Canola Sterol Esters | 6.000 |
| Solid Vitamin Premix | 2.000 |
| Vanilla Ice Cream Flavors | 0.750 |
| Soy Lecithin | 0.125 |
| Salt-Flour | 0.125 |

Milk Chocolate Chew:

| Ingredient | % Formula |
| --- | --- |
| Corn Syrup (63 D.E.) | 27.000 |
| Sugar - Cane or Beet | 21.000 |
| Sweetened Condensed Skim Milk | 15.000 |
| Milk Chocolate Liquor | 12.000 |
| Water | 8.000 |
| Cocoa Powder (10-12% fat) | 6.500 |
| Milled High CP Cocoa Extract | 1.500 |
| Canola Sterol Esters | 6.000 |
| Solid Vitamin Premix | 2.000 |
| Vanilla Ice Cream Flavors | 0.750 |
| Soy Lecithin | 0.125 |
| Salt-Flour | 0.125 |

The canola sterol esters used to prepare the chews are supplied by Raisio Benecol Ltd. of Finland or Raisio Staaco Inc. of the U.S. The esters have a melting point of about 30° C. and are heated at about 50-60° C. to ensure complete liquification. The phytosterols present in the mixture include B-sitosterol (50.6%), campesterol (27.6%), stigmasterol (16.8%). and other sterols (5%). The sterols are esterified using the inter-esterification process described in U.S. Pat. No. 5,502,045.

Having thus described in detail the preferred embodiments of the present invention, it is to be understood that the invention defined by the appended claims is not to be limited by any particular detail set forth in the above descriptions as many apparent variations thereof are possible without departing from the spirit or scope of the present invention.

What is claimed is:

1. A particulate milled cocoa extract comprising cocoa polyphenols including epicatechin, catechin, and procyanidin oligomers thereof, wherein the total cocoa polyphenol content is at least 300 milligrams per gram of the milled extract, and wherein the particulate milled cocoa extract is prepared by a process comprising the steps of i) defatting cocoa beans to obtain a partially or fully defatted cocoa powder, ii) solvent extracting the defatted cocoa powder to obtain a cocoa extract comprising cocoa polyphenols, iii) drying said extract, and iv) milling said extract to a mean particle size of less than about 15 microns and/or to where about 90 volume % of the milled extract particles are less than about 30 microns.

2. The extract of claim 1, wherein the total cocoa polyphenol content is about 300 milligrams to about 700 milligrams and wherein the mean particle size is less than about 10 microns and/or wherein about 90 volume % of the particles are less than about 20 microns.

3. The extract of claim 1, wherein the total cocoa polyphenol content is about 400 to about 600 milligrams and wherein the mean particle size is less than about 5 microns and/or wherein about 90 volume % of the particles are less than about 10 microns.

4. The extract of claim 3, wherein the total cocoa polyphenol content is about 400 to about 500 milligrams.

5. An additive consisting essentially of (i) a fat and/or an oil; (ii) a particulate milled cocoa extract according to claim 1; and (iii) optionally an emulsifier.

6. The additive of claim 5, wherein the fat is cocoa butter or a milk fat; wherein the oil is a vegetable oil; wherein the fat and/or the oil is present in an amount sufficient to disperse therein the milled cocoa extract; wherein the milled cocoa extract has a mean particle size of less than about 15 microns and/or wherein about 90 volume % of the particles are less than about 20 microns.

7. An additive consisting essentially of (i) a syrup comprising water and a nutritive carbohydrate sweetener and/or a sugar substitute; (ii) a particulate milled cocoa extract according to claim 1, and (iii) optionally a fat and/or an oil; wherein the syrup is present in an amount sufficient to disperse the milled cocoa extract therein.

8. The additive of claim 7, wherein the nutritive carbohydrate sweetener is a corn syrup or a blend thereof and another sweetener; wherein the total cocoa polyphenol content is about 400 milligrams to about 700 milligrams; wherein the mean particle size is less than about 10 microns and/or wherein about 90 volume % of the particles are less than about 20 microns; wherein the fat, if present, is cocoa butter or a milk fat; and wherein the oil, if present, is a vegetable oil.

9. The additive of claim 5 or 7, wherein the mean particle size is less than about 5 microns and/or wherein about 90 volume % of the particles are less than about 10 microns.

10. The additive of claim 5 or 7, wherein the mean particle size is less than about 5 microns and/or wherein about 90 volume % of the particles are less than about 10 microns.

11. A food, a medical food, a dietary supplement, or a pharmaceutical comprising (i) a particulate milled cocoa extract according to claim 1 and (ii) a fat, an oil, and/or a syrup.

12. The food of claim 11, wherein the food is a food having a continuous fat phase; an intermediate moisture food; an aerated food; a dry powder coating; a dry powder mix; or a baked food; wherein the fat is cocoa butter or a milk fat; wherein the oil is a vegetable oil; wherein the syrup is an aqueous solution of a nutritive carbohydrate sweetener and/or a sugar substitute; wherein the milled cocoa extract has a total cocoa polyphenol content of about 400 to about 700 milligrams per gram of the milled extract; and wherein the mean particle size of the milled cocoa extract is less than about 15 microns and/or wherein about 90 volume % of the particles are less than about 30 microns.

13. A chocolate which contains a milled cocoa extract according to claim 1.

14. The chocolate of claim 13, wherein the total cocoa polyphenol content is about 400 milligrams to about 700 milligrams; and wherein the mean particle size is less than about 10 microns and/or wherein about 90 volume % of the particles are less than about 20 microns.

15. The chocolate of claim 14, wherein the chocolate is a milk chocolate; wherein the total cocoa polyphenol content is about 400 to about 500 milligrams; and wherein the mean particle size is less than about 5 microns and/or wherein about 90 volume % of the particles are less than about 10 microns.

16. A method for preparing a high CP chocolate comprises the steps:
- (a) providing a mixture comprising one or more carbohydrate ingredients, one or more cocoa ingredients, and optionally one or more milk solids-containing ingredients; and
- (b) adding to the ingredient mixture, before, after, or during conching or refining, a particulate milled cocoa extract according to claim 1.

17. The chocolate of claim 13, which is selected from the group consisting of dark chocolate, bittersweet chocolate, baking chocolate, semi-sweet chocolate, sweet chocolate, milk chocolate, buttermilk chocolate, mixed dairy product chocolate, reduced fat chocolate, aerated chocolate, or compound coating chocolate.

* * * * *